(12) United States Patent
Thibodeau

(10) Patent No.: US 9,060,874 B2
(45) Date of Patent: Jun. 23, 2015

(54) SPINAL IMPLANT APPARATUS AND METHODS

(71) Applicant: Stryker Spine, Cestas (FR)

(72) Inventor: Lee L. Thibodeau, Cumberland, ME (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 14/199,493

(22) Filed: Mar. 6, 2014

(65) Prior Publication Data
US 2014/0188228 A1    Jul. 3, 2014

Related U.S. Application Data

(63) Continuation of application No. 13/491,944, filed on Jun. 8, 2012, now Pat. No. 8,690,926, which is a continuation of application No. 12/384,107, filed on Mar. 31, 2009, now Pat. No. 8,216,317.

(60) Provisional application No. 61/091,505, filed on Aug. 25, 2008, provisional application No. 61/040,821, filed on Mar. 31, 2008.

(51) Int. Cl.
*A61B 17/88*    (2006.01)
*A61F 2/44*    (2006.01)
(Continued)

(52) U.S. Cl.
CPC .............. *A61F 2/447* (2013.01); *A61F 2/4455* (2013.01); *A61F 2/4611* (2013.01);
(Continued)

(58) Field of Classification Search
CPC ......... A61F 2/44; A61F 2/4405; A61F 2/442; A61F 2/46; A61F 2/4603; A61B 17/562; A61B 2017/564; A61B 2017/567; A61B 17/56

USPC .......... 606/246, 248, 249, 99, 86 A, 279, 96, 606/104; 623/17.11–17.16
See application file for complete search history.

(56) References Cited

U.S. PATENT DOCUMENTS

| 4,714,469 A | 12/1987 | Kenna |
| 5,649,931 A | 7/1997 | Bryant et al. |

(Continued)

FOREIGN PATENT DOCUMENTS

| EP | 1752116 A1 | 2/2007 |
| WO | 2007050322 A1 | 5/2007 |
| WO | 2010011849 A1 | 1/2010 |

OTHER PUBLICATIONS

Extended European Search Report for Application No. 11829818.1 dated Jun. 6, 2014.

*Primary Examiner* — Ellen C Hammond
*Assistant Examiner* — Christina Negrellirodrigue
(74) *Attorney, Agent, or Firm* — Lerner, David, Littenberg, Krumholz & Mentlik, LLP

(57) ABSTRACT

A method of inserting and positioning an intervertebral spacer is provided. The spacer includes a longitudinal axis, an on-axis interface coincident with or parallel to the longitudinal axis, and an off-axis interface angled to the longitudinal axis. The spacer's front end may be curved. The method may include inserting the spacer into the disc space utilizing a tool to engage an on-axis interface and then to engage one or more of the off-axis interfaces, which may be used for further modification of the spacer. The tool is moved substantially along a single insertion direction, which may be substantially parallel to a posterior-anterior axis of the disc space. The method may result in the longitudinal axis of the spacer being perpendicular to the insertion direction, or substantially parallel to a medial-lateral axis of the disc space. The spacer may also be positioned in an anterior aspect of the disc space.

18 Claims, 16 Drawing Sheets

(51) Int. Cl.
  *A61F 2/46* (2006.01)
  *A61F 2/30* (2006.01)
(52) U.S. Cl.
  CPC ............... *A61F 2002/30133* (2013.01); *A61F 2002/30281* (2013.01); *A61F 2002/30507* (2013.01); *A61F 2002/30518* (2013.01); *A61F 2002/30538* (2013.01); *A61F 2002/3054* (2013.01); *A61F 2002/30579* (2013.01); *A61F 2002/30604* (2013.01); *A61F 2002/30617* (2013.01); *A61F 2002/4628* (2013.01); *A61F 2002/4629* (2013.01); *A61F 2220/0025* (2013.01); *A61F 2230/0015* (2013.01); *A61F 2230/0086* (2013.01); *A61F 2250/0006* (2013.01); *A61F 2250/0097* (2013.01); *A61F 2310/00023* (2013.01)

(56) References Cited

U.S. PATENT DOCUMENTS

| | | | |
|---|---|---|---|
| 5,782,830 | A | 7/1998 | Farris |
| 6,066,174 | A | 5/2000 | Farris |
| 6,562,072 | B1 | 5/2003 | Fuss et al. |
| 6,579,318 | B2 | 6/2003 | Varga et al. |
| 6,613,090 | B2 | 9/2003 | Fuss et al. |
| 6,699,288 | B2 | 3/2004 | Moret |
| 6,719,794 | B2 | 4/2004 | Gerber et al. |
| D493,225 | S | 7/2004 | Varga et al. |
| 6,764,491 | B2 | 7/2004 | Frey et al. |
| D494,274 | S | 8/2004 | Varga et al. |
| 6,830,570 | B1 | 12/2004 | Frey et al. |
| D501,555 | S | 2/2005 | Varga et al. |
| 6,852,127 | B2 | 2/2005 | Varga et al. |
| 6,984,245 | B2 | 1/2006 | McGahan et al. |
| 6,987,245 | B2 | 1/2006 | Sanpei et al. |
| 7,060,073 | B2 | 6/2006 | Frey et al. |
| 7,060,096 | B1 | 6/2006 | Schopf et al. |
| 7,137,997 | B2 | 11/2006 | Paul |
| 7,226,483 | B2 | 6/2007 | Gerber et al. |
| 7,235,082 | B2 | 6/2007 | Bartish et al. |
| 7,361,193 | B2 | 4/2008 | Frey et al. |
| 7,470,273 | B2 | 12/2008 | Dougherty-Shah |
| 7,479,160 | B2 | 1/2009 | Branch et al. |
| 7,481,812 | B2 | 1/2009 | Frey et al. |
| 7,500,991 | B2 | 3/2009 | Bartish, Jr. et al. |
| 7,575,580 | B2 | 8/2009 | Lim et al. |
| 7,591,852 | B2 | 9/2009 | Prosser |
| 7,632,281 | B2 | 12/2009 | Errico et al. |
| 7,635,371 | B2 | 12/2009 | McGahan et al. |
| 7,658,766 | B2 | 2/2010 | Melkent et al. |
| 7,806,932 | B2 | 10/2010 | Webb et al. |
| 7,976,549 | B2 | 7/2011 | Dye et al. |
| 2002/0065560 | A1 | 5/2002 | Varga et al. |
| 2003/0060886 | A1 | 3/2003 | Van Hoeck et al. |
| 2004/0030346 | A1 | 2/2004 | Frey et al. |
| 2004/0186574 | A1 | 9/2004 | Varga et al. |
| 2004/0186575 | A1 | 9/2004 | Varga et al. |
| 2005/0096745 | A1 | 5/2005 | Andre et al. |
| 2005/0283244 | A1 | 12/2005 | Gordon et al. |
| 2005/0283245 | A1 | 12/2005 | Gordon et al. |
| 2006/0004376 | A1 | 1/2006 | Shipp et al. |
| 2006/0178746 | A1 | 8/2006 | Bartish et al. |
| 2006/0212119 | A1 | 9/2006 | Varga et al. |
| 2006/0212120 | A1 | 9/2006 | McGahan et al. |
| 2006/0229627 | A1 | 10/2006 | Hunt et al. |
| 2006/0235426 | A1 | 10/2006 | Lim et al. |
| 2006/0241761 | A1 | 10/2006 | Gately |
| 2007/0067035 | A1 | 3/2007 | Falahee |
| 2007/0073400 | A1 | 3/2007 | Paul |
| 2007/0073405 | A1 | 3/2007 | Verhulst et al. |
| 2007/0093850 | A1 | 4/2007 | Harris et al. |
| 2007/0093897 | A1 | 4/2007 | Gerbec et al. |
| 2007/0118223 | A1 | 5/2007 | Allard et al. |
| 2007/0142843 | A1 | 6/2007 | Dye |
| 2007/0162128 | A1 | 7/2007 | DeRidder et al. |
| 2007/0208343 | A1 | 9/2007 | Magerl et al. |
| 2007/0213737 | A1 | 9/2007 | Schermerhorn et al. |
| 2007/0213826 | A1* | 9/2007 | Smith et al. ............... 623/17.11 |
| 2007/0225726 | A1 | 9/2007 | Dye et al. |
| 2007/0225808 | A1 | 9/2007 | Warnick |
| 2007/0243255 | A1 | 10/2007 | Xu et al. |
| 2007/0255415 | A1 | 11/2007 | Edie et al. |
| 2007/0282441 | A1 | 12/2007 | Stream et al. |
| 2008/0009880 | A1 | 1/2008 | Warnick et al. |
| 2008/0058933 | A1 | 3/2008 | Garner et al. |
| 2008/0065082 | A1 | 3/2008 | Chang et al. |
| 2008/0065219 | A1 | 3/2008 | Dye |
| 2008/0077150 | A1 | 3/2008 | Nguyen |
| 2008/0077153 | A1 | 3/2008 | Pernsteiner et al. |
| 2008/0077241 | A1 | 3/2008 | Nguyen |
| 2008/0091211 | A1 | 4/2008 | Gately |
| 2008/0097435 | A1 | 4/2008 | DeRidder et al. |
| 2008/0097454 | A1 | 4/2008 | DeRidder et al. |
| 2008/0109005 | A1 | 5/2008 | Trudeau et al. |
| 2008/0119935 | A1 | 5/2008 | Alvarez |
| 2008/0140085 | A1 | 6/2008 | Gately et al. |
| 2008/0221694 | A1 | 9/2008 | Warnick et al. |
| 2008/0224694 | A1 | 9/2008 | Bidenbach et al. |
| 2008/0255574 | A1 | 10/2008 | Dye |
| 2008/0262623 | A1 | 10/2008 | Bagga et al. |
| 2008/0269901 | A1 | 10/2008 | Baynham et al. |
| 2008/0281424 | A1 | 11/2008 | Parry et al. |
| 2008/0287957 | A1 | 11/2008 | Hester et al. |
| 2008/0306488 | A1 | 12/2008 | Altarac et al. |
| 2008/0306489 | A1 | 12/2008 | Altarac et al. |
| 2009/0030423 | A1 | 1/2009 | Puno |
| 2009/0054991 | A1 | 2/2009 | Biyani et al. |
| 2009/0105832 | A1 | 4/2009 | Allain et al. |
| 2009/0105836 | A1 | 4/2009 | Frey et al. |
| 2009/0112217 | A1 | 4/2009 | Hester |
| 2009/0112220 | A1 | 4/2009 | Kraus |
| 2009/0138055 | A1 | 5/2009 | Altarac et al. |
| 2009/0143829 | A1 | 6/2009 | Shluzas |
| 2009/0143859 | A1 | 6/2009 | McClellan, III et al. |
| 2009/0157186 | A1 | 6/2009 | Magerl |
| 2009/0177285 | A1 | 7/2009 | Frey et al. |
| 2009/0187246 | A1 | 7/2009 | Foley |
| 2009/0198246 | A1 | 8/2009 | Lim et al. |
| 2009/0222092 | A1 | 9/2009 | Davis et al. |
| 2009/0228110 | A1 | 9/2009 | McClintock |
| 2009/0234364 | A1 | 9/2009 | Crook |
| 2009/0248163 | A1 | 10/2009 | King et al. |
| 2009/0299479 | A1 | 12/2009 | Jones et al. |
| 2010/0094422 | A1 | 4/2010 | Hansell et al. |
| 2010/0137922 | A1 | 6/2010 | Hunt et al. |
| 2010/0191337 | A1 | 7/2010 | Zamani et al. |
| 2012/0245696 | A1* | 9/2012 | Thibodeau ............... 623/17.16 |

* cited by examiner

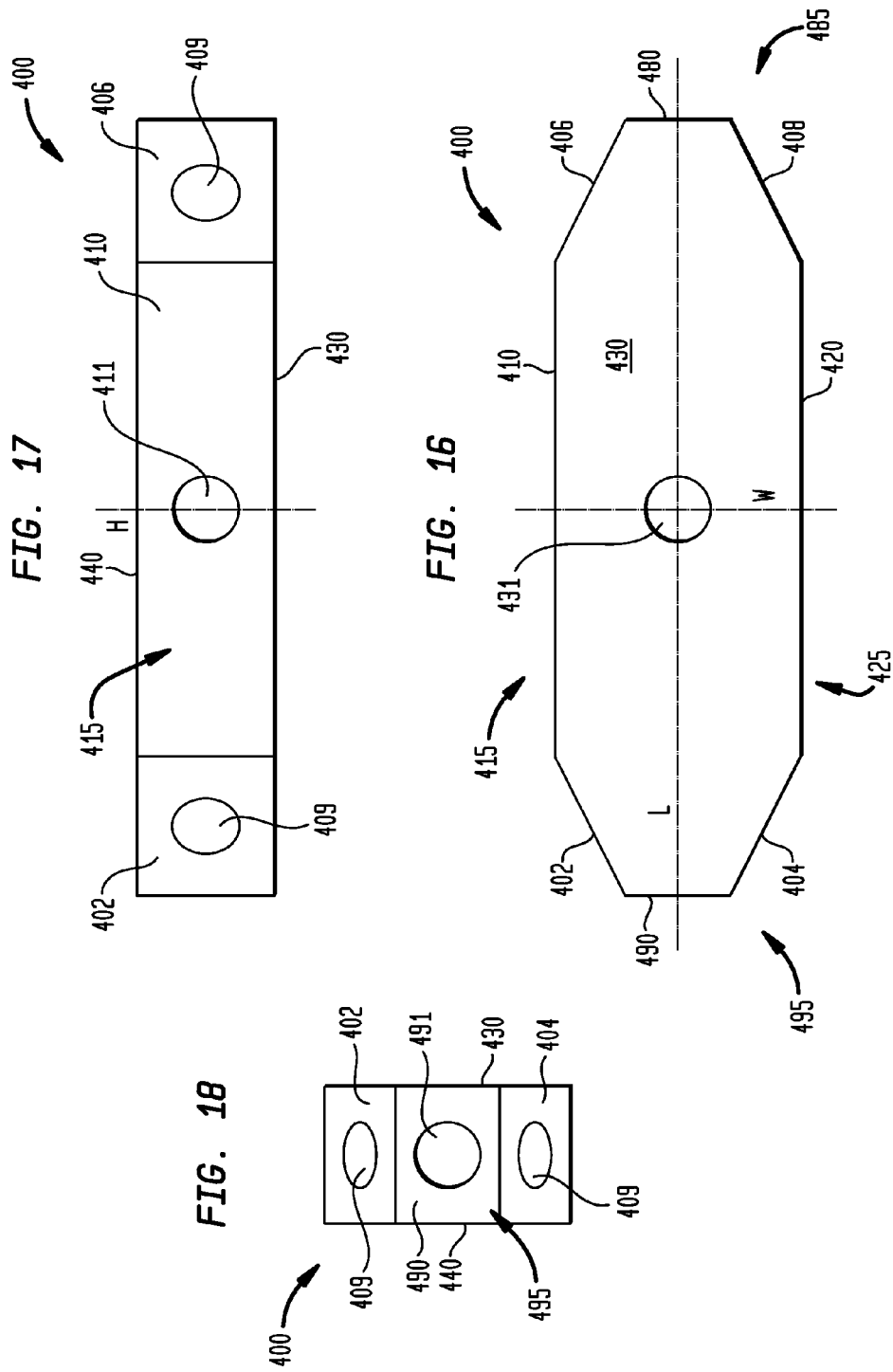

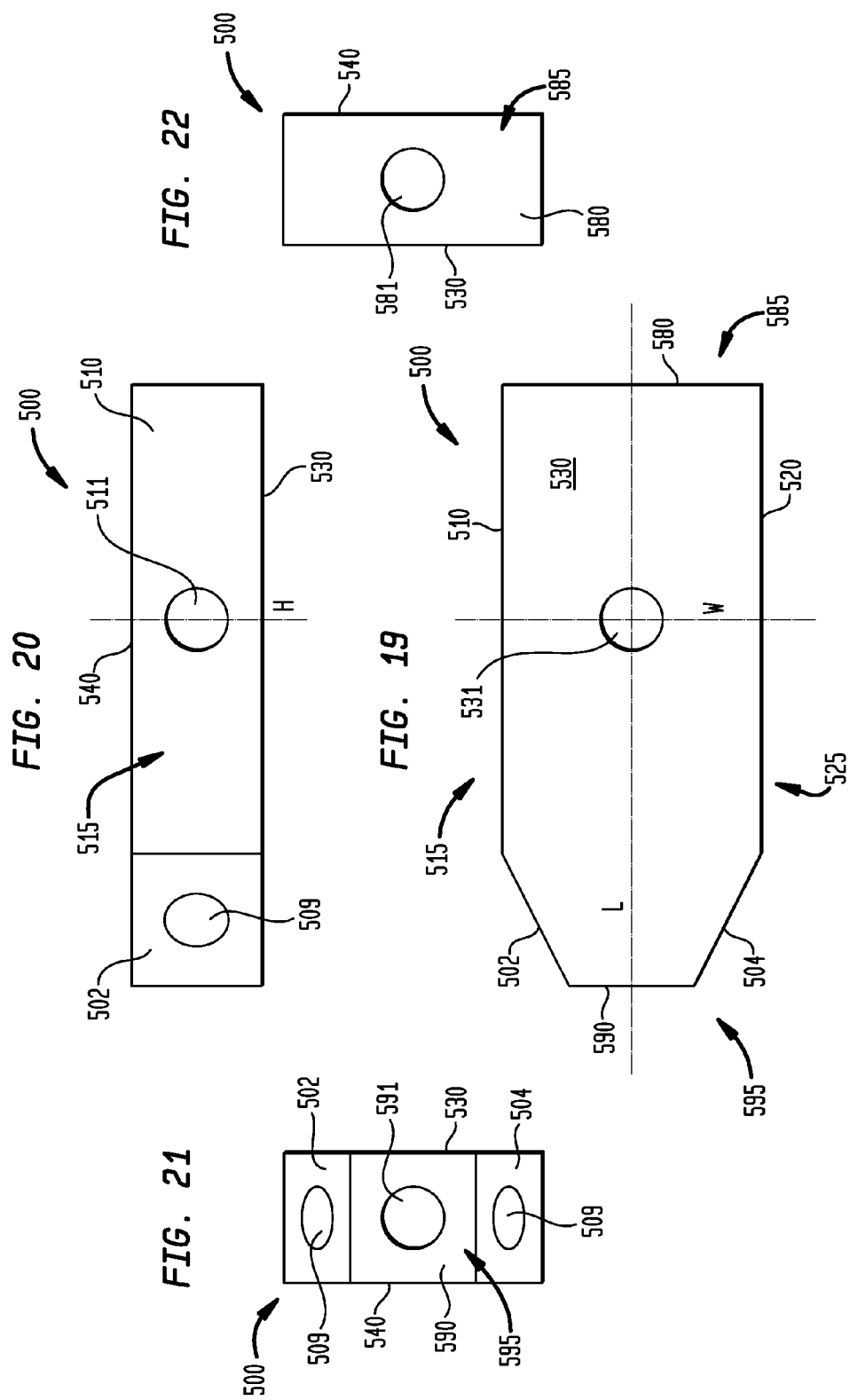

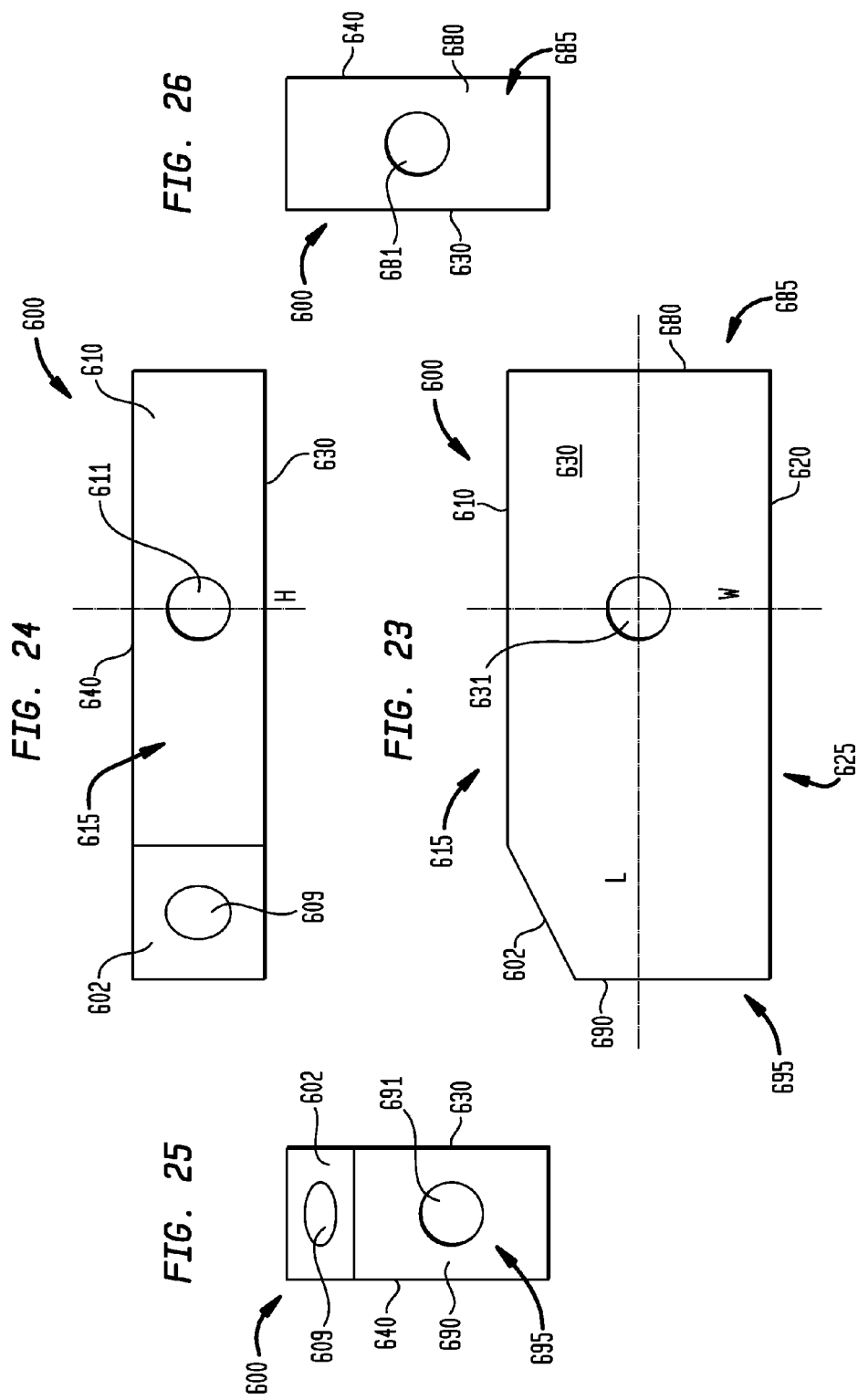

SPINAL IMPLANT APPARATUS AND METHODS

CROSS-REFERENCE TO RELATED APPLICATIONS

The present application is a continuation of U.S. patent application Ser. No. 13/491,944, filed Jun. 8, 2012, which is a continuation of U.S. patent application Ser. No. 12/384,107, now U.S. Pat. No. 8,216,317, filed Mar. 31, 2009, which claims the benefit of U.S. Provisional Patent Application No. 61/040,821, filed on Mar. 31, 2008, and U.S. Provisional Patent Application No. 61/091,505 filed on Aug. 25, 2008, the disclosures of which are hereby incorporated herein by reference.

BACKGROUND OF THE INVENTION

The present invention relates to a spinal implant apparatus and a method of using that apparatus to treat a spine disorder. More particularly, the present invention relates to an implant apparatus, which includes a steerable spacer and a manipulation device or positioning tool, and a method for using the positioning tool to position the spacer at a desirable position at the anterior region of a vertebra. Further, the present invention relates to an intervertebral spacer arranged for selectable steerage to a location of interest between adjacent vertebrae, and a mechanism to manipulate or alter the apparatus in an off-axis manner.

Back pain can be caused by any one of several problems that affect the intervertebral discs of the spine. These problems include, for example, degeneration, bulging, herniation, thinning of a disc, or abnormal movement, and the pain that is experienced generally is attributable to friction or pressure that inevitably occurs when one adjacent vertebra exerts uneven pressure, or when both adjacent vertebrae exert such pressure, on the disc. Back pain may also be attributed to neural element injury.

Whenever an individual suffers from a disc problem, a typical remedy is to perform interbody, intervertebral, cervical, thoracic, or lumbar fusion (all generically referred to herein as "IF") surgery on the patient for the purpose of fusing together the two vertebrae that flank the defective disc to form a single, solid bone mass. Existing IF techniques generally involve removing the offending disc from the patient, adding bone graft material into the interbody space between the flanking vertebrae, and inserting a spinal implant device into that space to hold the graft material in place and to support the flanking vertebrae while solid bone mass forms.

Existing IF techniques fail to enable fine positioning of an implant device with respect to the vertebrae. A brief discussion of the basic anatomy of the human spine, and specifically, the lumbar vertebrae of the spine, will help better illustrate this limitation. FIG. 1 is a partial representation of the lumbar region of a human spine, in which an intervertebral disc 10 is arranged between a superior vertebra 20 and an inferior vertebra 30. Specifically, disc 10 is positioned between a bottom surface 21 of superior vertebra 20 and a top surface 31 of inferior vertebra 30. FIG. 2 is a top view of inferior vertebra 30, which includes top surface 31 of a vertebral body 32. Vertebral body 32 is formed by a cortical rim 33, which is a dense, hard shell that is formed by compact bone, and an end plate portion 34 formed by much softer and less compact end plate material, or cancellous bone.

Referring to FIG. 3, existing IF procedures, including those associated with the lumbar region, involve positioning at least one spinal implant 50 so that it is substantially centered between end plate portion 34 of inferior vertebra 30 and an end plate portion 24 on bottom surface 21 of superior vertebra 20. Such positioning of implant 50 does not promote lordosis. Further, in this position, implant 50 tends to depress upon, or even become embedded in, end plate portion 34 of inferior vertebra 30 and/or end plate portion 24 of superior vertebra 20. This settling of implant 50 is referred to as subsidence, during which the vertebrae-supporting properties of implant 50 are reduced or eliminated. The result may be less than desirable coronal and/or sagittal alignment of the spine.

Existing IF procedures are further limited in other ways. During IF surgery, the surgeon must navigate a spinal implant device through a region that is densely packed with neural elements, muscle, ligaments, tendons and bone to access top surface 31 of inferior vertebra 30. In existing IF techniques, this requires extensive cutting and/or manipulation of this region, which can extend patient recovery time and subject the patient to other side effects, such as, for example, inflammation, which can be discomforting. Worse, in some patients, the patient must be entered in two or three of at least three possible body areas (i.e., the patient's posterior region in a posterior interbody fusion technique, the patient's anterior region in an anterior interbody fusion technique, the patient's lateral region in a lateral interbody fusion technique, and/or the patient's transforaminal region in a transforaminal interbody fusion technique) for the purpose of positioning the spinal implant device. More generally, existing IF techniques are substantially invasive and can be difficult to perform.

Further, a limitation of existing tools used in IF procedures relates to the design of the spinal implant device. In some IF procedures, locating the spinal implant device in the position of interest cannot be done by hand alone. Instead, a tool is required to push the spinal implant device to the position of interest, particularly when lordosis promotion is the goal of the IF procedure. Present spinal implant devices are configured so that their interface with the positioning tool occurs only along or parallel to the primary longitudinal axis, one of the orthogonal axes, of the spinal implant device. The primary longitudinal axis generally coincides with anterior or posterior directions of insertion. For example, certain presently used spinal implant devices are rectangular in shape and include a port that is centrally and parallelly aligned with the primary longitudinal axis of the spinal implant device used to releasably receive the positioning tool therein. As a result, such a spinal implant device (herein referred to as an "on-axis" spinal implant device) can only be moved and/or guided by the positioning tool in a straight line along its primary axis. If the on-axis spinal implant device is not initially aligned directly with its ultimate intervertebral location, or if it shifts during travel, it will not reach its ultimate position of interest without considerable effort and time to ensure that the on-axis spinal implant device is as close to the position of interest as possible. Even then, the surgeon can generally only approximate that position. Therefore, the configuration of current on-axis spinal implant devices limits a surgeon's ability to place the spinal implant device effectively.

What is needed, therefore, is a spinal implant apparatus and method of using the apparatus that enable a surgeon to easily, consistently, and effectively position a prosthetic intervertebral spacer substantially at the anterior region of an intervertebral disc space, i.e. between the cortical rims of adjacent vertebrae, with as minimal an impact on the patient as possible. Such an apparatus would decrease patient risk, speed recovery and substantially improve success rates in terms of restoration of normal spinal confirmation and neurological decompression.

SUMMARY OF THE INVENTION

It is an object of the present invention to provide an apparatus for treating a patient in need of IF surgery. The apparatus specifically enables a surgeon to position a spacer to a desirable position. The present apparatus is a spacer including one or more off-axis contact sites and, optionally, one or more on-axis contact sites. For purposes of description of the present invention, "off-axis" means a steerage, directional and/or expansion contact location that is anywhere part of the spacer except at a location that is aligned with the primary longitudinal axis of the spacer. An off-axis location may include any non-orthogonal location, as well as orthogonal locations except for the primary longitudinal axis of the spacer. The contact sites are arranged for releasable interfacing with a steering and/or expansion tool and to enable fine and minimally invasive manipulation within the patient for positioning the spacer at the desirable location. The spacer includes a primary rectangular shape but is not limited thereto. In one or more embodiments, the spacer includes one or more chamfered corners or sections, which may be of rectangular shape. One or more of the one or more chamfered corners may include a tool interface, such as a port arranged to allow for releasable insertion of a tool insert. Alternatively or additionally, one or more of the one or more chamfered corners may include a nodule or pin that may be releasably joined to a tool interface. The spacer may thusly be configured to enable its steerage from a starting location to the desirable location at more than just straight-line movements using a positioning tool of interest. Instead, the spacer may be moved at 30°, 45°, or any other angles of interest with respect to the axis of insertion, including orthogonal angles other than on the primary longitudinal axis of the spacer.

Further, in an embodiment of the spacer including a curved front end, the off-axis interface arrangement enables the surgeon to move the spacer in an arc if that is deemed to be a suitable means of traversal. For example, the spacer front end may be configured in a shape that causes it to have a higher frictional characteristic interface with the end plate (or vertebral body surface) while the back end may have a lower frictional characteristic at that interface. Such a design enables a type of sliding motion of the spacer when pushed off-axis. The present invention is applicable in any type of spinal surgery. While the focus of the discussion of a preferred embodiment of the present invention is directed to lumbar IF surgery, it is to be understood that the invention may be employed in cervical and thoracic spinal procedures, as well as from any direction, i.e., anterior, posterior, and lateral.

In one example, the steerable spacer further includes a plurality of surfaces and a plurality of ports that are formed partially within, or entirely through, the plurality of surfaces. The plurality of ports may be located at selectable positions on one or more surfaces of the spacer, and, preferably, but not essentially, at least two of the ports are located on two surfaces that are at the rear end, and, preferably, but not essentially, at least one of the ports is on a surface that is not located at the rear end.

The present invention not only provides one or more devices and related methods for off-axis spacer positioning, it also provides for off-axis alteration of the size and/or shape of a spacer, such as with an expandable spacer (cage), for example. In particular, then, the present invention establishes one or more interbody distracting devices and related tool usage to enable the off-axis modification or alteration of the position, size and/or shape of such interbody distracting devices. The one or more devices may include one or more on-axis features, but do include one or more off-axis features.

The present invention is constructed to decrease patient risk, speed recovery, and substantially improve success rates in terms of restoration of normal spinal confirmation and neurological decompression. This is achieved by providing the surgeon with a spacer that is much more readily movable into an intervertebral position deemed best suited for the patient's condition and, possibly, altered in size, dimension and/or shape to further improve the implant's clinical result. These and other advantages of the present invention will become apparent upon review of the following description and accompanying drawings.

A first aspect of the present invention is a method of inserting and positioning a prosthetic intervertebral spacer in the intervertebral disc space between two adjacent vertebrae comprising the steps of providing a spacer including a longitudinal axis, an on-axis interface, and an off-axis interface, the on-axis interface being coincident with or parallel to the longitudinal axis, and the off-axis interface being angled with respect to the longitudinal axis, engaging a tool to the on-axis interface, inserting the spacer at least partially into the intervertebral disc space by moving the tool substantially along an insertion direction, engaging the tool to the off-axis interface, and inserting the spacer further into the intervertebral disc space by moving the tool substantially along the insertion direction, such that the longitudinal axis of the spacer is angled with respect to the insertion direction.

In accordance with certain embodiments of this first aspect, the insertion direction may be substantially parallel to a posterior-anterior axis of the intervertebral disc space. The method may further include the steps of engaging the tool to a second off-axis interface of the spacer, and inserting the spacer further into the intervertebral disc space by moving the tool substantially along the insertion direction. The combination of the inserting steps may result in the longitudinal axis of the spacer being perpendicular to the insertion direction. The longitudinal axis of the spacer may be substantially parallel to a medial-lateral axis of the intervertebral disc space. The inserting steps may result in the spacer being positioned in an anterior aspect of the intervertebral disc space. The inserting steps may include allowing the spacer to rotate with respect to the insertion direction. The spacer may further include a front end having frictional properties that are greater than frictional properties of a rear end of the spacer, and the inserting steps may include allowing the front end to turn within the intervertebral disc space as it frictionally engages one or both of the adjacent vertebrae. The on-axis and off-axis interfaces may be ports, the tool may include a retractable member, and the engaging steps may include placing the retractable member in the respective ports. The combination of the inserting steps may result in the longitudinal axis of the spacer being rotated approximately 90 degrees with respect to the insertion direction. The method may further include the step of packing bone grafting material into at least one of the on-axis interface, the off-axis interface, and an opening in the spacer. The method may further include the step of expanding the spacer.

A second aspect of the present invention is a method of inserting and positioning a prosthetic intervertebral spacer in the intervertebral disc space between two adjacent vertebrae comprising the steps of providing a spacer including a curved front end, a longitudinal axis, an on-axis interface, and an off-axis interface, wherein the on-axis interface is coincident with or parallel to the longitudinal axis, and wherein the off-axis interface is angled with respect to the longitudinal axis, establishing a connection between a tool and the spacer, the connection being at the on-axis interface, inserting the spacer at least partially into the intervertebral disc space by moving the tool substantially along an insertion direction, relocating the connection to the off-axis interface, and inserting the spacer further into the intervertebral disc space by moving the tool substantially along the insertion direction, such that the spacer rotates with respect to the insertion direction.

In accordance with certain embodiments of this second aspect, the method may further include the steps of engaging the tool to a second off-axis interface of the spacer, and inserting the spacer further into the intervertebral disc space by moving the tool substantially along the insertion direction. The combination of the inserting steps may result in the longitudinal axis of the spacer being perpendicular to the insertion direction. The inserting steps may result in the spacer being positioned in an anterior aspect of the intervertebral disc space. The spacer may further include a front end having frictional properties that are greater than frictional properties of a rear end of the spacer, and the inserting steps may include allowing the front end to turn within the intervertebral disc space as it frictionally engages one or both of the adjacent vertebrae. The on-axis and off-axis interfaces may be ports, the tool may include a retractable member, and the establishing step may include placing the retractable member in the respective ports.

A third aspect of the present invention is a method of inserting and positioning a prosthetic intervertebral spacer in the intervertebral disc space between two adjacent vertebrae comprising the steps of providing a spacer including a longitudinal axis, an on-axis interface, and an off-axis interface, the on-axis interface being coincident with or parallel to the longitudinal axis, and the off-axis interface being angled with respect to the longitudinal axis, applying a first force to the on-axis interface to move the spacer in the intervertebral disc space, and applying a second force to the off-axis interface to further move the spacer in the intervertebral disc space, wherein the first and second forces are provided by a tool moving substantially along a single direction and the first and second forces cause the spacer to rotate.

In accordance with certain embodiments of this third aspect, the spacer may further include a front end having frictional properties that are greater than frictional properties of a rear end of the spacer, and the applying steps may include allowing the front end to turn within the intervertebral disc space as it frictionally engages one or both of the adjacent vertebrae.

A fourth aspect of the present invention is a method of inserting and positioning a prosthetic intervertebral spacer in the intervertebral disc space between two adjacent vertebrae comprising the steps of providing a spacer including a longitudinal axis and an off-axis interface being angled with respect to the longitudinal axis, providing a tool for use in expanding the spacer, engaging the tool to the off-axis interface, and expanding the spacer.

A fifth aspect of the present invention is a prosthetic intervertebral spacer comprising a longitudinal axis, an on-axis interface being coincident with or parallel to the longitudinal axis, an off-axis interface being angled with respect to the longitudinal axis, a front end including a beveled edge, and a rear end having an on-axis chamfered section being perpendicular to the longitudinal axis and an off-axis chamfered section being angled with respect to the longitudinal axis.

In accordance with certain embodiments of this fifth aspect, the front end may be curved with respect to the longitudinal axis. The on-axis interface may be disposed on the on-axis chamfered section and the off-axis interface may be disposed on the off-axis chamfered section. The front end may have frictional properties and the rear end may have frictional properties, the frictional properties of the front end being greater than the frictional properties of the rear end.

BRIEF DESCRIPTION OF THE DRAWINGS

FIG. 16 is a top view of another embodiment of a spacer of the present invention, the bottom being a mirror image thereof.

FIG. 17 is a first side view of the spacer of FIG. 16, the second side being a mirror image thereof.

FIG. 18 is a rear view of the spacer of FIG. 16, the front being a mirror image thereof.

FIG. 19 is a top view of another embodiment of a spacer of the present invention, the bottom being a mirror image thereof.

FIG. 20 is a first side view of the spacer of FIG. 19, the second side being a mirror image thereof.

FIG. 21 is a rear view of the spacer of FIG. 19.

FIG. 22 is front view of the spacer of FIG. 19.

FIG. 23 is top view of another embodiment of a spacer of the present invention, the bottom being a mirror image thereof.

FIG. 24 is a first side view of the spacer of FIG. 23.

FIG. 25 is a rear view of the spacer of FIG. 23.

FIG. 26 is a front view of the spacer of FIG. 23.

DETAILED DESCRIPTION

Figure 3:
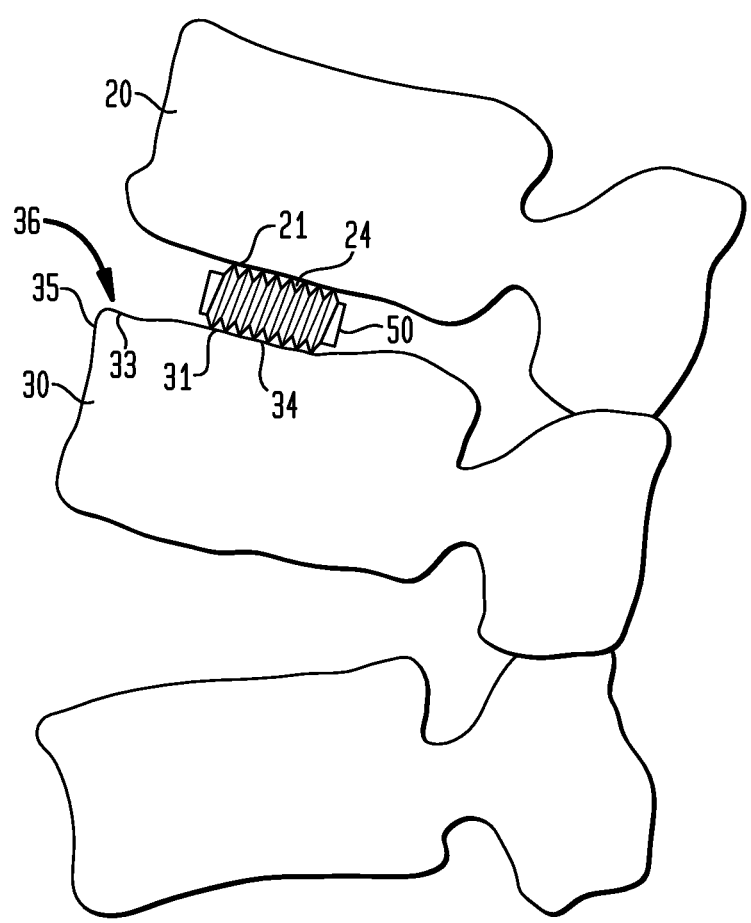
FIG. 3 is a side view similar to FIG. 1 showing an existing spinal implant device positioned between the end plate portions of the inferior and superior vertebrae.
Figure 4:
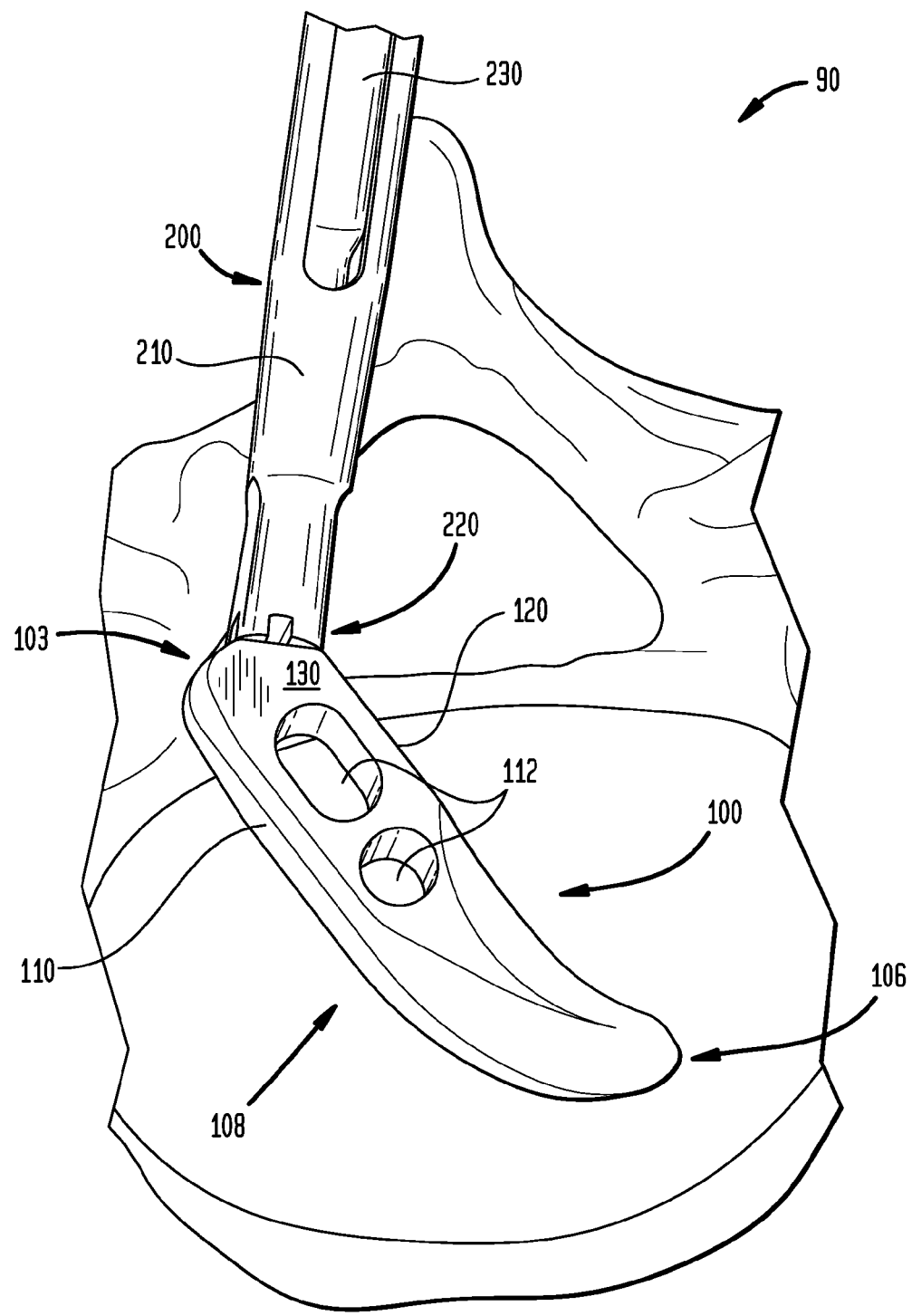
FIG. 4 is a perspective view of an apparatus of the present invention including a spacer and a positioning tool removably connected to the spacer.
Figure 5:
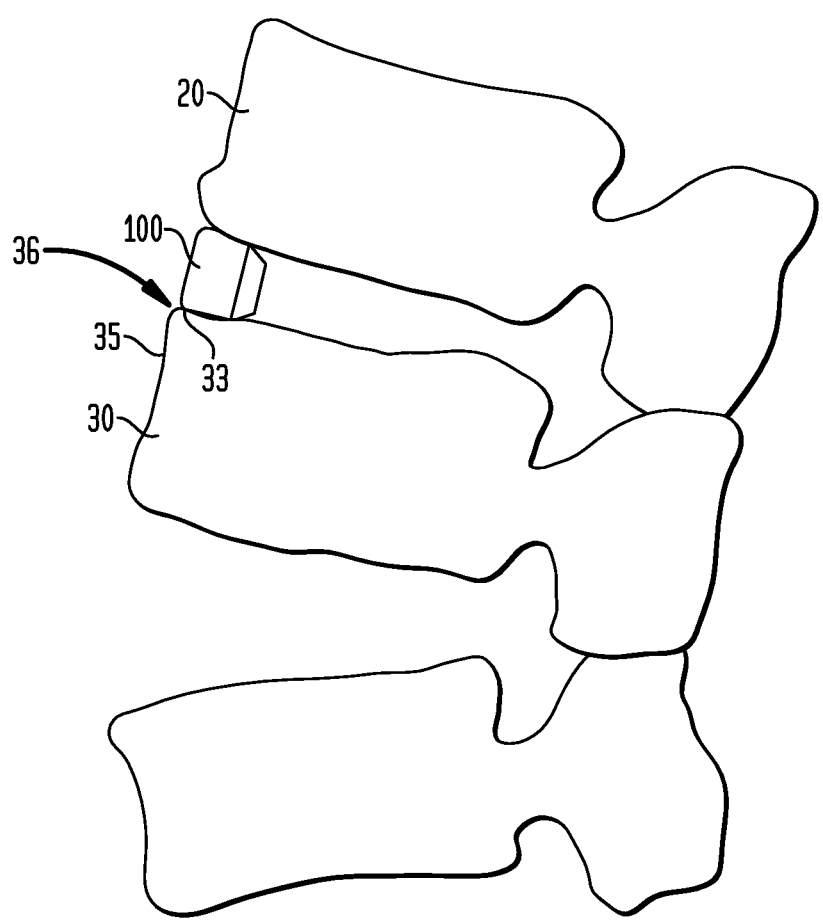
FIG. 5 is a side view similar to FIG. 1 showing a spacer of the present invention positioned near the anterior regions and substantially between the cortical rims of inferior and superior vertebrae.

Referring to FIG. 4, a spinal implant apparatus 90 of the present invention includes a prosthetic intervertebral spacer 100 and a positioning tool 200 for fine and minimally invasive manipulation of spacer 100 within a patient in need of lumbar interbody fusion ("LIF") surgery. Apparatus 90 allows spacer 100 to be easily and consistently positioned to a desirable location 36 as represented in FIG. 5, where desirable location 36 is near the anterior region 35 of inferior vertebra (a similar desirable location located near the anterior region of superior vertebra 20). Therefore, spacer 100 is shown in FIG. 5 as being positioned substantially between the upper surface of cortical rim 33 of inferior vertebra 30 and the lower surface of the cortical rim of superior vertebra 20. Positioned in desirable location 36, spacer 100 is maximally supported by cortical rim 33 (and a like cortical rim of superior vertebra 20), and spacer 100 better promotes alignment and lordosis than it would if it were located substantially adjacent to end plate portion 34 (see FIG. 3) or anywhere else along inferior vertebra 30.

Figure 6:
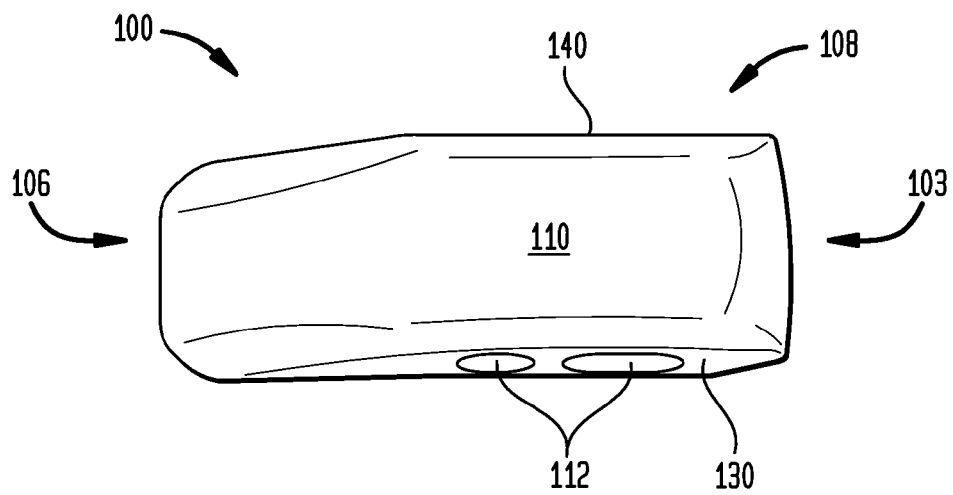
FIG. 6 is a first side view of the spacer of FIG. 4.
Figure 7:
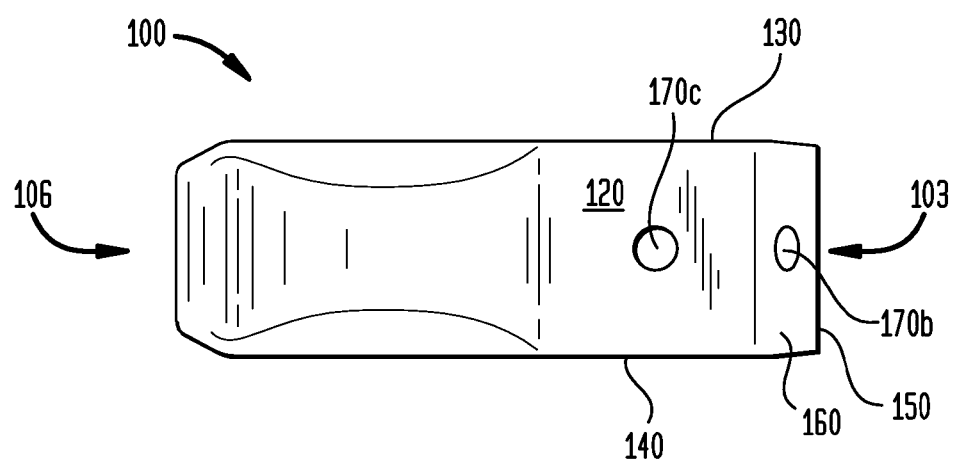
FIG. 7 is a second side view of the spacer of FIG. 4.

Referring to FIGS. 6 and 7, spacer 100 is in a single, integral form. It is to be understood, however, that spacer 100 is not limited to being in a single, integral form. Therefore, spacer 100 may be formed of a plurality of parts, with any particular part being either removably connectable to, or being permanently fixed to, any other particular part. Further, spacer 100 may be of any selectable shape provided it is configured to allow for its forced movement into a selectable position at desirable location 36. Further, spacer 100 may be expandable to allow the surgeon to fine tune lordosing adjustment.

Figure 8:
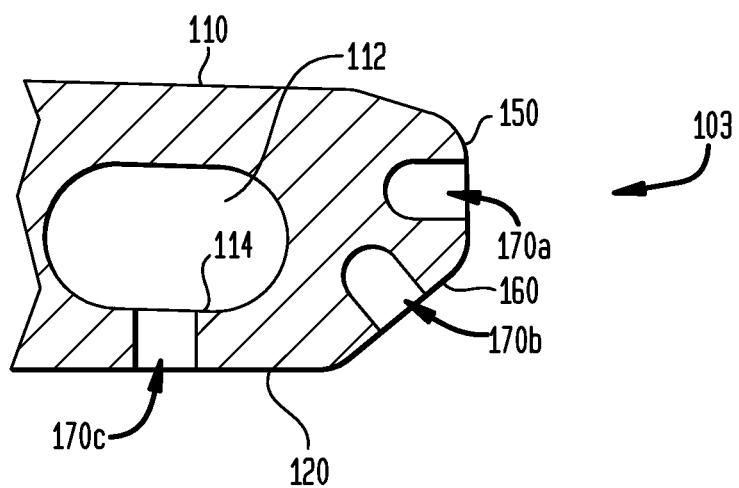
FIG. 8 is a partial cross-sectional top view of a rear end of the spacer of FIG. 4.

Spacer 100 includes a plurality of surfaces, which include a top surface 130, a bottom surface 140, a first side surface 110, a second side surface 120, a first spacer contact surface 150, and a second spacer contact surface 160. One or more openings 112 are optionally formed through top surface 130 and/or bottom surface 140 and may extend fully therebetween. First spacer contact surface 150 and second spacer contact surface 160 are at a rear end 103 of spacer 100, spaced opposite from a front end 106 by a body region 108. Each one of second side surface 120, first spacer contact surface 150, and second spacer contact surface 160 includes a port 170 (shown as ports 170a-c in FIG. 8). Port 170a is located on first contact surface 150. Port 170b is located on second contact surface 160. Port 170c is located on second side surface 120. It is to be understood, however, that spacer 100 is not limited to having any one or more of ports 170a, 170b, or 170c. Spacer 100 may therefore include none, one, or two of ports 170a, 170b, and 170c, and it may include one or more additional ports 170 at one or more other surfaces of spacer 100 that may not necessarily be second side surface 120, first spacer contact surface 150, or second spacer contact surface 160. Further, referring to FIG. 8, any particular port 170 may be formed as extending partially into spacer 100 (e.g., ports 170a and 170b formed within surfaces 150 and 160, respectively) or completely through spacer 100 from one surface to another (e.g., port 170c formed completely through second side surface 120 and an interior surface 114 of opening 112).

Front end 106 and bottom surface 140 of spacer 100 are designed specifically to enable steerable movement of spacer 100 to desirable location 36 when spacer 100 is moved along top surface 31 of inferior vertebra 30. In the embodiment shown in FIG. 4, front end 106 is of curved form, as it is preferably inserted such that the curved portion of front end 106 points toward the medial portion of the intervertebral disc space. Although shown curved only in its front end, the spacer according to the present invention may be curved along one or more portions or the entirety of the body region of the spacer. Front end 106 may be of different dimensions than rear end 103. Front end 106 may also be beveled or otherwise shaped to increase its friction with respect to top surface 31 so that it is inclined to dig into the cancellous bone and be forced to turn in a direction associated with the direction of its curved form. That is, the area at or adjacent to the curved form of front end 106 produces greater friction between inferior vertebra 30 and bottom surface 140 (as shown best in FIG. 7), than is produced between the area at or adjacent to rear end 103 of bottom surface 140 and inferior vertebra 30. Accordingly, the same could be true for top surface 130 with respect to superior vertebra 20. The increased frictional properties may be determined by the height or shape of spacer 100 at front end 106 relative to the height of the disc space, or may be due to roughened or textured surfaces of front end 106 adjacent inferior vertebra 30 and superior vertebra 20. More specifically, the curved nature of front end 106 or its overall shape may provide or supplement the frictional aspects of front end 106. Other known methods may also be used to increase the friction to a desired level. The increased frictional properties of spacer 100 at front end 106 are advantageous for positioning spacer 100 on top surface 31 of inferior vertebra 30, as will be described with regard to the method of insertion, presented below.

Figure 9:
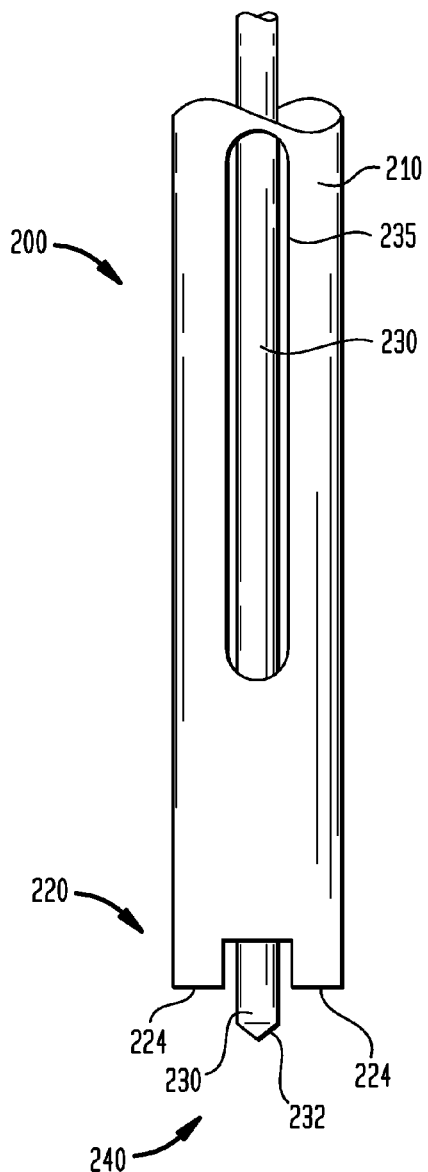
FIG. 9 is a side view of a portion of the positioning tool of FIG. 4.
Figure 10:
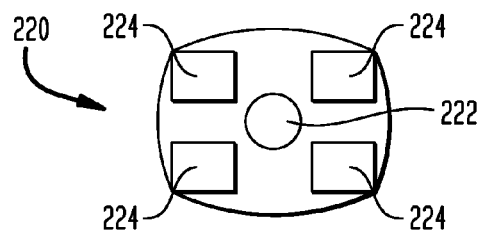
FIG. 10 is a front view of the positioning tool of FIG. 4.

An exemplary positioning tool 200 that may be used for releasable joining to any of the positioning interfaces described herein, e.g. ports 170, is shown in FIGS. 9 and 10. It is to be understood that positioning tool 200 is a generic insertion tool or device, and that other similar tools or devices may be used. Other devices may be employed for the purpose of causing movement of any of the spacers described herein. Positioning tool 200 includes a housing member 210, a spacer contact portion 220, and a retractable member 230 that is contained within, and is movable within, housing member 210. Retractable member 230 includes a tip 232 that is arranged for securable, but removable, insertion within any of interface ports 170 of spacer 100, or any other spacer herein described. Retractable member 230 may be flexible, yet of sufficient rigidity to maintain its insertion into port 170 while allowing a spacer connected to positioning tool 200 to move or pivot with respect to the longitudinal axis of positioning tool 200. Housing member 210 may include an optional cutaway section 235 for viewing retractable member 230, and therefore for viewing any movement of retractable member 230, within housing member 210. Along these lines, retractable member 230 may be marked with indicia such that the surgeon can tell of its longitudinal displacement with respect to housing member 210. At least a portion of retractable member 230 is extendable beyond an opening 222 of contact surface 220, to a position such as position 240, which is outside housing member 210 near contact surface 220. The skilled artisan will recognize that there are a number of options for designing positioning tool 200 such that retractable member 230 is capable of being moved within, and to a position outside of, housing member 210. In addition to opening 222, contact portion 220 includes at least one contact surface 224 for contacting spacer 100.

The skilled artisan will recognize that a spacer and a positioning tool according to the present invention may be formed from any one or more of a plurality of materials. Regardless of the material used to form the spacer, that material or materials should have physical properties sufficient to allow it to withstand the rigors of being manipulated by a positioning tool during surgery, and to remain intact and in the preferred position, e.g., desirable location 36, within the harsh environment that is the human spine. Materials that may be used to form the spacer and/or the positioning tool include, but are not limited to, non-metallic materials, such as polymer materials, including polyetherketone (PEK), polyetherketoneketone (PEKK), polyetheretherketone (PEEK), polyetherketoneetherketoneketone (PEKEKK), or a combination thereof, for example, and metallic materials, such as titanium and alloys including titanium, for example.

A method of insertion according to the present invention may be carried out for the purpose of treating a patient who is experiencing an intervertebral disc problem, such as degeneration, bulging, herniation, and/or thinning, of a disc of the lumbar region of a spine, for example. The method generally includes steps for using positioning tool 200 to position spacer 100 substantially between the outer, dense portion of a vertebra and the vertebra that is adjacent and superior to that vertebra, from which an intervertebral disc has been surgically removed. Specifically, the method allows for a 360° fusion of these inferior and superior vertebrae with minimal disruption of the surrounding soft tissue in, and minimal bone removal from, the patient. Therefore, the method is minimally invasive. However, it is contemplated that the method may be carried out as part of a surgery that is not entirely minimally invasive.

Before any of the steps of the method of insertion are to be carried out, it is expected that the patient will undergo a plurality of preparation steps. These preparation steps may include, but are not limited to being, those steps that are generally taken by those skilled in the art of performing a standard unilateral or bilateral decompressive laminectomy. These steps therefore optionally may include sparing the facet joints, which are directly over the nerve roots of the spine, and removing soft tissue from those joints. These steps may further optionally include accessing a disc that is to be removed or otherwise treated on its symptomatic side (in the case of scoliosis, for example, this would be the concave side) and removing all or a portion of that disc. Other steps performed at or near this time optionally may include inserting one or more pedicle screws at one or more desired locations (e.g., in the L4 and L5 pedicles), inserting a disc space distractor and distracting the disc space by any one or more techniques for doing so that are known to the skilled artisan. Still further, other steps at this time optionally may include carrying out a radical discectomy, which may include preparing end plates for fusion, removing soft tissue along the anterior and lateral rims of the disc space, and packing graft material anteriorally, and/or contralaterally, in that space.

Figure 11:
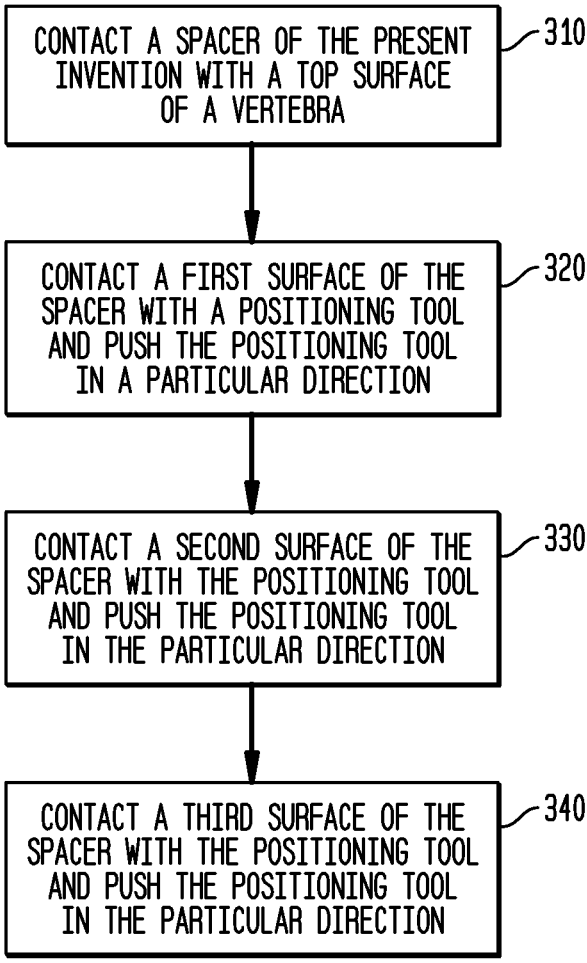
FIG. 11 is a flow diagram of the steps of a method of inserting a spacer according to the present invention.
Figure 12:
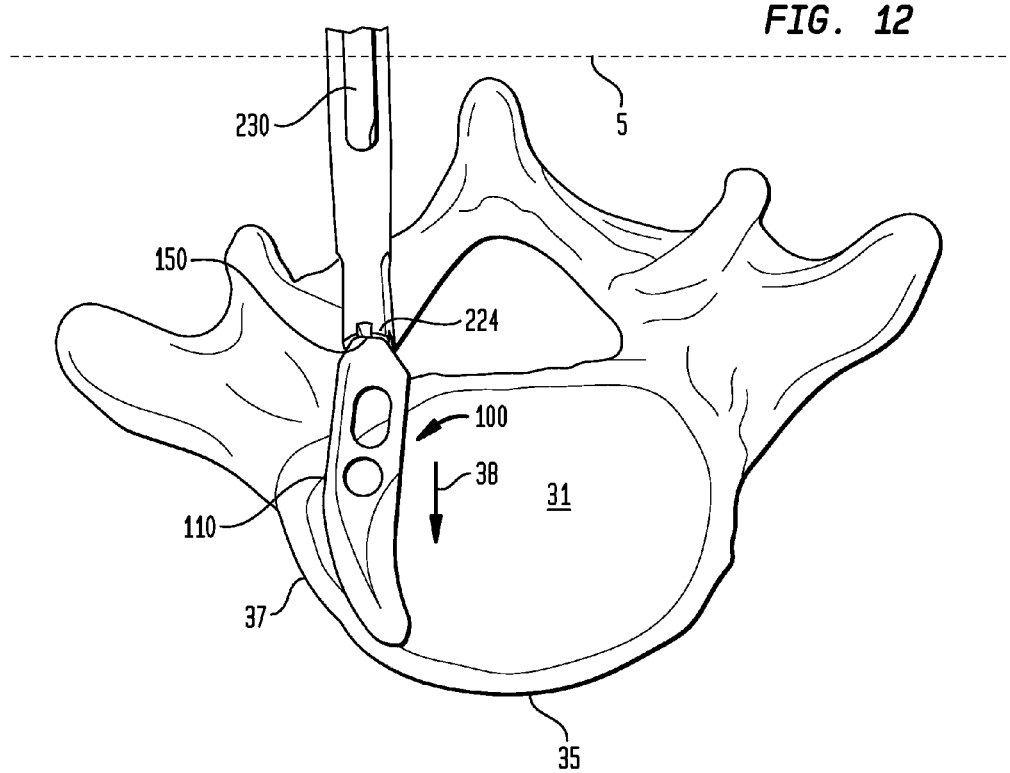
FIGS. 12-14 are top perspective views depicting a method of inserting and positioning the spacer according to the present invention.
Figure 13:
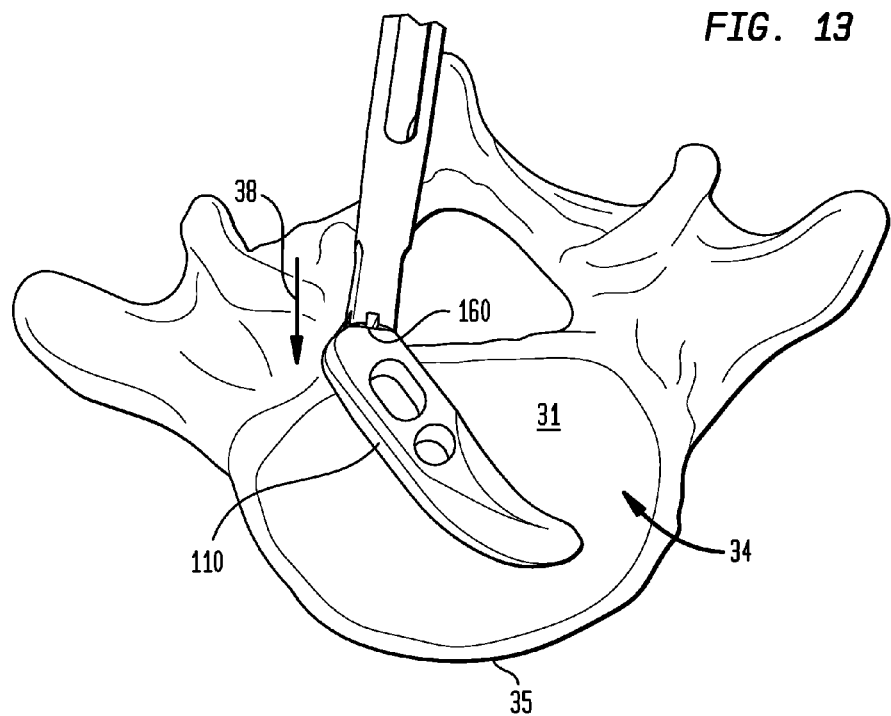
Figure 14:
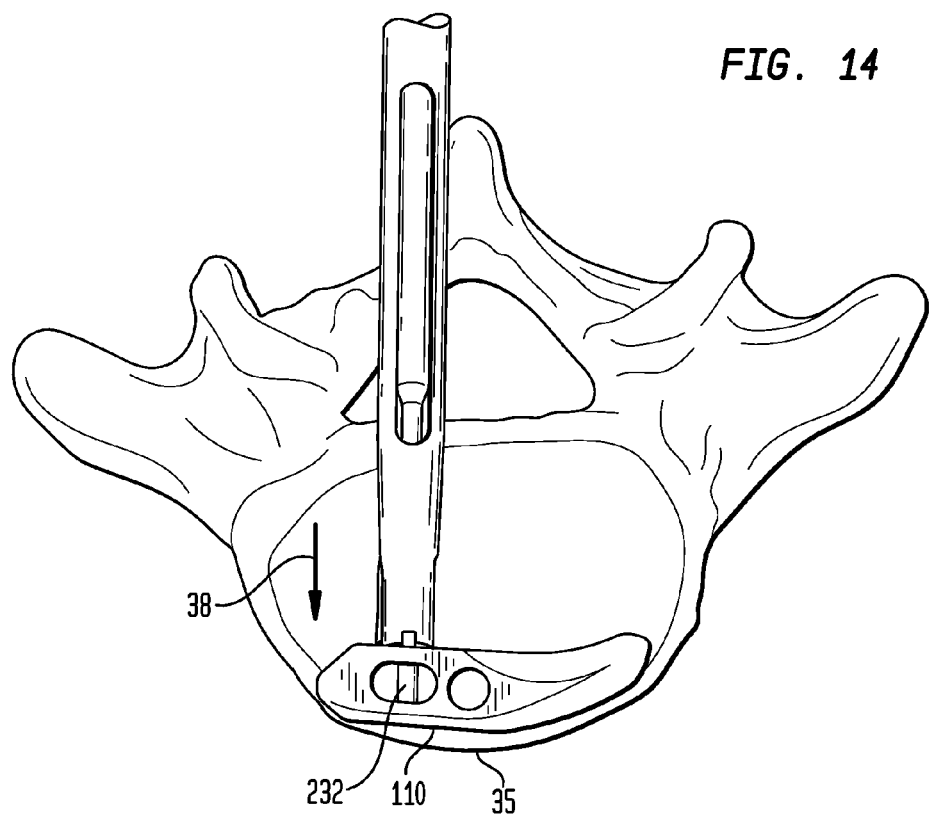

In a specific embodiment, which is outlined in the flow diagram of FIG. 11 and depicted in FIGS. 12-14, a method 300 includes a step 310 of passing spacer 100 through a patient's back 5 and contacting bottom surface 140 of spacer 100 to inferior vertebra 30 at top surface 31. FIG. 12 shows spacer 100 positioned on top surface 31 of inferior vertebra 30 after spacer 100 has been passed through patient's back 5. Step 310 is preferably carried out by using positioning tool 200. For example, tip 232 of positioning tool 200 may be securably and removably inserted into port 170a of first spacer contact surface 150 of spacer 100, while spacer 100 is outside the patient, or at least outside the patient's spine, and then moved onto top surface 31. Alternatively, positioning tool 200 could be engaged with spacer 100 subsequent to a partial insertion of spacer 100 in the patient's spine. In this regard, a separate tool could be utilized to partially insert spacer 100.

After spacer 100 is contacted to top surface 31, a step 320 is carried out wherein spacer 100 is oriented such that it is positioned at a side region 37 of top surface 31 at a substantially right angle with respect to anterior region 35 of top surface 31 by placing tip 232 of retractable member 230 into port 170a of first contact surface 150, and/or contacting contact surface 224 to first contact surface 150, and moving spacer 100 substantially in a direction 38 along top surface 31 by moving positioning tool 200 substantially in direction 38. FIG. 12 shows spacer 100 at side region 37 and substantially at a right angle with respect to anterior region 35 of inferior vertebra 30 after spacer 100 has been moved into that position by using positioning tool 200.

Next, a step 330 is carried out wherein spacer 100 is oriented such that spacer 100 is positioned substantially at end plate portion 34 of inferior vertebra 30 at an angle that is not substantially a right angle with respect to anterior region 35 of inferior vertebra 30, by inserting tip 232 into port 170b of second contact surface 160, and/or contacting contact surface 224 to second contact surface 160, and then moving spacer 100 substantially in direction 38, for example, along top surface 31 by moving positioning tool 200 substantially in direction 38. FIG. 13 shows spacer 100 in position at the cancellous bone portion, or end plate portion 34, at an angle that is not substantially a right angle with respect to anterior region 35 after spacer 100 has been moved into that position by using the positioning tool 200. Specifically, during step 330, due to the increased frictional characteristics of spacer 100 at front end 106, rear end 103 of spacer 100 moves more freely in direction on top surface 31 of inferior vertebra 30 compared to the movement of front end 106. Thus, spacer 100 tends to turn according to its curved profile. This turning tends to reorient spacer 100 such that its longitudinal axis moves toward a parallel orientation with respect to anterior region 35, i.e. a medial-lateral axis of the adjacent vertebra. In addition, at this stage of method 300, front end 106 reaches the stiffer cortical rim 33 where it can move or slide more easily than it can on the softer cancellous bone, or end plate portion 34.

Next, a step 340 is carried out wherein spacer 100 is moved into a position that is near and substantially parallel to anterior region 35, approximating desirable location 36 upon cortical rim 33 of inferior vertebra 30. This is achieved by inserting tip 232 into port 170c of second side surface 120, and/or contacting contact surface 224 to second side surface 120, and then moving spacer 100 along top surface 31 by moving positioning tool 200 in direction 38. FIG. 14 shows spacer 100 substantially at desirable location 36.

It is important to note that the curved nature of spacer 100 along with its differently angled ports 170 allow for posterior insertion of spacer 100 to desirable location 36. That is, a linear tool such as positioning tool 200 is all that is necessary to rotate spacer 90° with respect to top surface 31. This is made possible through the configuration of spacer 100 itself. More specifically, as the configuration of front end 106 curves spacer 100 during insertion, different ports 170 are exposed to the posterior insertion site, and thus are exposed for manipulation by positioning tool 200. Tip 232 may therefore be inserted into a port 170, and as spacer 100 tends to curve during insertion, tip 232 may be removed from port 170 and contact surface 224 may be utilized to further push, and therefore rotate, spacer 100. This will, in turn, expose another port 170, which may be utilized by positioning tool 200 as insertion continues. This cooperation between the curving nature of spacer 100 and the re-positioning of positioning tool 200 with respect to rear end 103 of spacer and ports 170 makes it possible to posteriorly insert a longitudinal spacer, such as spacer 100, into a position such as desirable location 36, which is along a medial-lateral axis of the intervertebral disc space. Moreover, all of this is accomplished while only moving tool 200 in direction 38.

Figure 15:
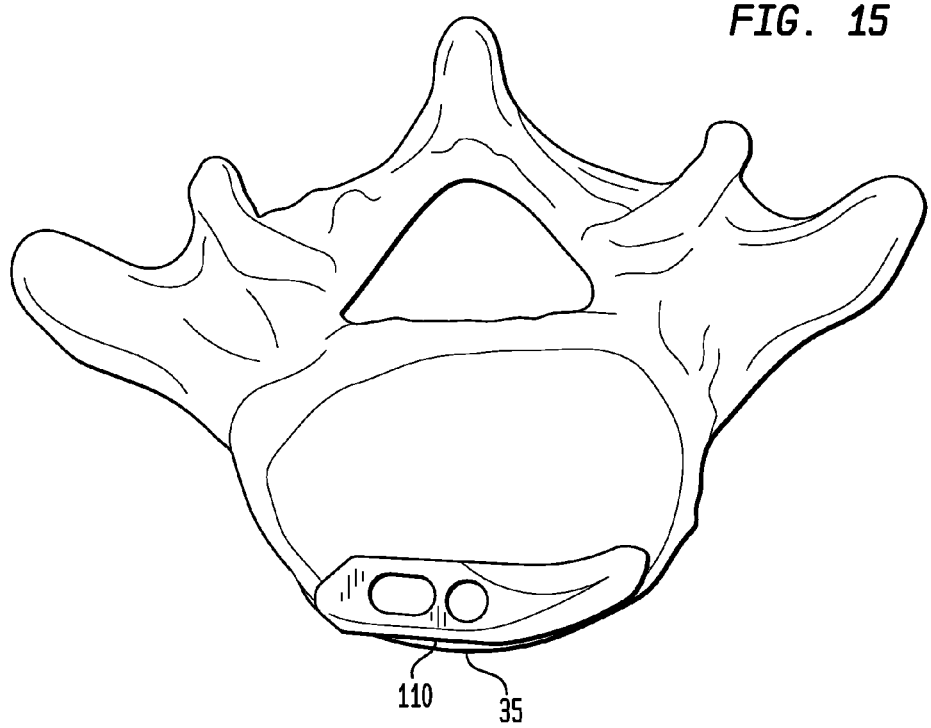
FIG. 15 is a top perspective view of the spacer positioned in a desirable location according to the method depicted in FIGS. 12-14.

FIG. 15 shows spacer 100 at desirable location 36 after positioning tool 200 has been removed from the patient. It is a goal of method 300 for spacer 100 to remain at desirable location 36 after method 300 has been carried out. The skilled artisan will recognize that there are a number of options for securing spacer 100 at its ultimate location, i.e. desirable location 36. For example, one or more expandable set screws may be used to secure spacer 100. When one or more set screws are used in this fashion, it is expected that spacer 100 will expand by a small amount, such as several millimeters, for example. When spacer 100 so expands, it is expected that lordosis will be effected or will be further effected, anterior distraction will be enhanced, and openings 112 within spacer 100 will expand to allow for addition of graft material into openings 112.

Further, it is to be understood that although method 300 has been described herein with respect to steps 310-340, one or more variations may be made to method 300. For example, a surgeon carrying out method 300 may elect to use two positioning tools 200 concomitantly while carrying out one or more of positioning steps 310-340 of method 300. The surgeon therefore may, for example, insert tip 232 of one positioning tool 200 into port 170a and tip 232 of a second positioning tool 200 into port 170b, and then position spacer 100 essentially according to step 320 of method 300 before then positioning spacer 100 essentially according to step 330 of method 300, while throughout this procedure, tips 232 remain within ports 170a, 170b, respectively. Alternatively, a single positioning tool may be arranged to enable complete steerage of spacer 100 to desirable location 36 without disconnecting the positioning tool from spacer 100.

Further embodiments of a spacer according to the present invention will now be described, each spacer having one or more off-axis positioning interface sites. There are a plurality of embodiments of the spacer, wherein each includes one or more positioning interface sites at a location or locations on the body of the spacer that are not aligned with or parallel to the primary longitudinal axis of the spacer. In addition to being beneficial for the precise positioning of the spacer, the at least one off-axis interface may be utilized as the only interface for modification of the spacer, or as an interface for further modification of the spacer after the use of one or more other interfaces. The modification can be for expansion or size alteration, which will be further discussed below. Such further modification may take place after the spacer is finally positioned or at any stage during the insertion process. In general, as shown in FIGS. 16-17, a spacer used in an IF procedure may be characterized as having a primary longitudinal length axis L, a width axis W, and a height axis H, each being an orthogonal axis of the spacer. The terms "on-axis" and "off-axis" will be herein referred to as describing their relation to longitudinal length axis L of a spacer. An "on-axis" port, for example, is one that is aligned with or parallel to length axis L, whereas an "off-axis" port, for example, is one that is not aligned with or parallel to length axis L. A spacer according to the present invention preferably includes at least one on-axis positioning interface site and at least one off-axis positioning interface site. An off-axis positioning interface site may include, but is not limited to, non-orthogonal locations and at, along, or parallel to either or both of width axis W and height axis H.

The existence of at least one off-axis positioning interface site of the body of the spacer of the present invention provides the surgeon with the opportunity to direct the placement of the spacer at something other than straight ahead longitudinal movement, i.e. along a posterior-anterior axis. A positioning tool may be removably joined to the spacer at an interface site and manipulated to cause movement of the spacer. Further, the tool may remain attached to the spacer and be realigned in an off-axis manner. When the positioning tool is joined to, or realigned with respect to, the spacer at an off-axis interface and the tool is moved, the spacer moves at an angle with respect to the alignment of the positioning tool, which angle may be orthogonal or non-orthogonal. That is to say that the spacer tends to move along an axis of the positioning tool, regardless of the location at which the positioning tool is connected to the spacer. Thus, the length axis L of the spacer may be angled with respect to the axis of the positioning tool during such insertion. The result is that a surgeon may advantageously manipulate the spacer with finer control than has been available with the existing spacers.

FIGS. 16-18 illustrate another embodiment of an off-axis spacer 400 of the present invention. Spacer 400 includes a top surface 430, a bottom surface 440 that is preferably a mirror image of top surface 430, first and second sides 415 and 425, respectively, that are mirror images of one another, a front end 485, and a rear end 495 that is preferably a mirror image of front end 485. First side 415 includes a first side surface 410, and second side 425 includes a second side surface 420. Similarly, front end 485 includes a front surface 480, and rear end 495 includes a rear surface 490. Top surface 430 includes an optional top interface port 431 configured and arranged for releasably connecting to a positioning tool, such as aforementioned positioning tool 200. Top interface port 431 may be a smooth bore hole, a threaded hole, or a slotted hole. Top interface port 431 may or may not extend completely through from top surface 430 to bottom surface 440. Alternatively, spacer 400 may be constructed such that it includes one or more connecting elements in addition to or instead of top interface port 431 that may be a rod, a hook, or any other means rather than a port for releasably joining to a positioning tool. It is to be noted that bottom surface 440 may also include such an interface, there may be fewer than or more than one interface at either or both of top surface 430 and bottom surface 440, and there may be different numbers of connecting means at top surface 430 and bottom surface 440. Spacer 400 may be fabricated as a unitary structure or it may be fabricated of a plurality of sections. It may be of fixed dimensions or expandable. It may be fabricated of one or more materials of interest, provided such material is selected to enable spacer 400 to perform for its intended purpose under the expected conditions.

It is to be noted that top interface port 431 is an off-axis axial interface. That is, it is not aligned or in parallel with length axis L. Rather, in this instance, top interface port 431 is parallel to non-primary height axis H. Top surface 430 and bottom surface 440 of spacer 400 are those surfaces that contact the adjacent vertebrae and establish the spacing surfaces of spacer 400 and their separation from one another establishes the height of spacer 400. Placement of an interface on either top surface 430 or bottom surface 440 is optional, but does provide the surgeon with flexibility in at least the initial stages of spacer placement. Of course, it is to be understood that there may be through holes (not shown) extending from top surface 430 to bottom surface 440 to allow for bone graft packing and growth therethrough to secure spacer 400 in position as part of the IF procedure.

Spacer 400 further includes a plurality of chamfered sections. First chamfered section 402 and second chamfered section 404 are located at rear end 495 of spacer 400, while third chamfered section 406 and fourth chamfered section 408 are located at front end 485 of spacer 400. Further, first chamfered section 402 and third chamfered section 406 are located at first side 415 of spacer 400, while second chamfered section 404 and fourth chamfered section 408 are located at second side 425 of spacer 400. First chamfered section 402 is spaced from and connected to second chamfered section 404 by rear surface 490 of spacer 400, and third chamfered section 406 is spaced from and connected to fourth chamfered section 408 by front surface 480 of spacer 400. In addition, first chamfered section 402 is spaced from and connected to third chamfered section 406 by first side surface 410 of spacer 400, and second chamfered section 404 is spaced from and connected to fourth chamfered section 408 by second side surface 420 of spacer 400.

Figure 1:
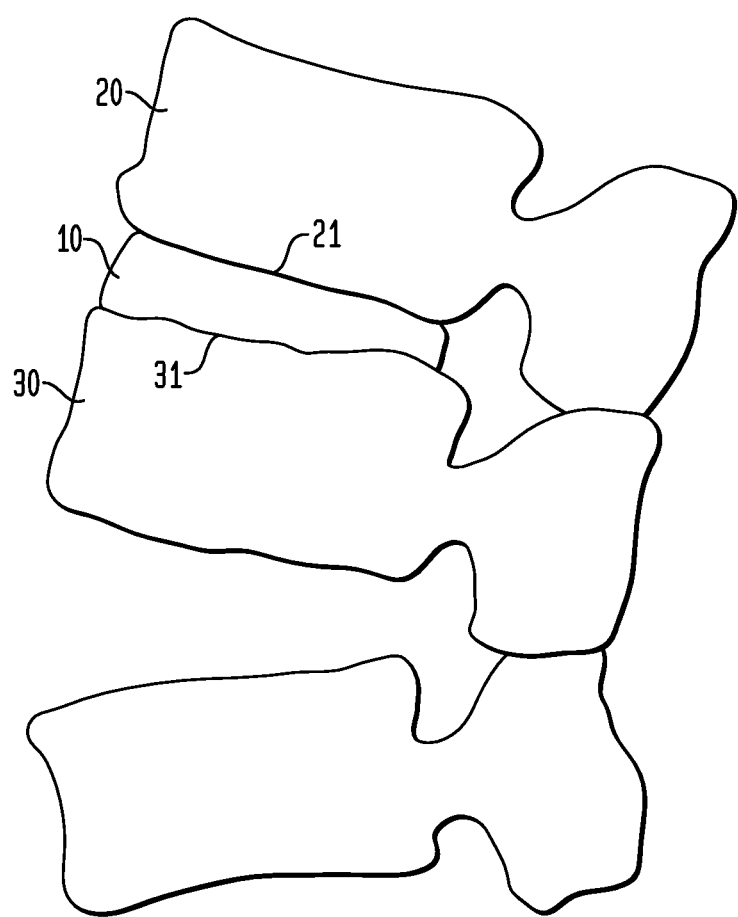
FIG. 1 is a side view of a partial spinal arrangement of an intervertebral disc and two vertebrae.
Figure 2:
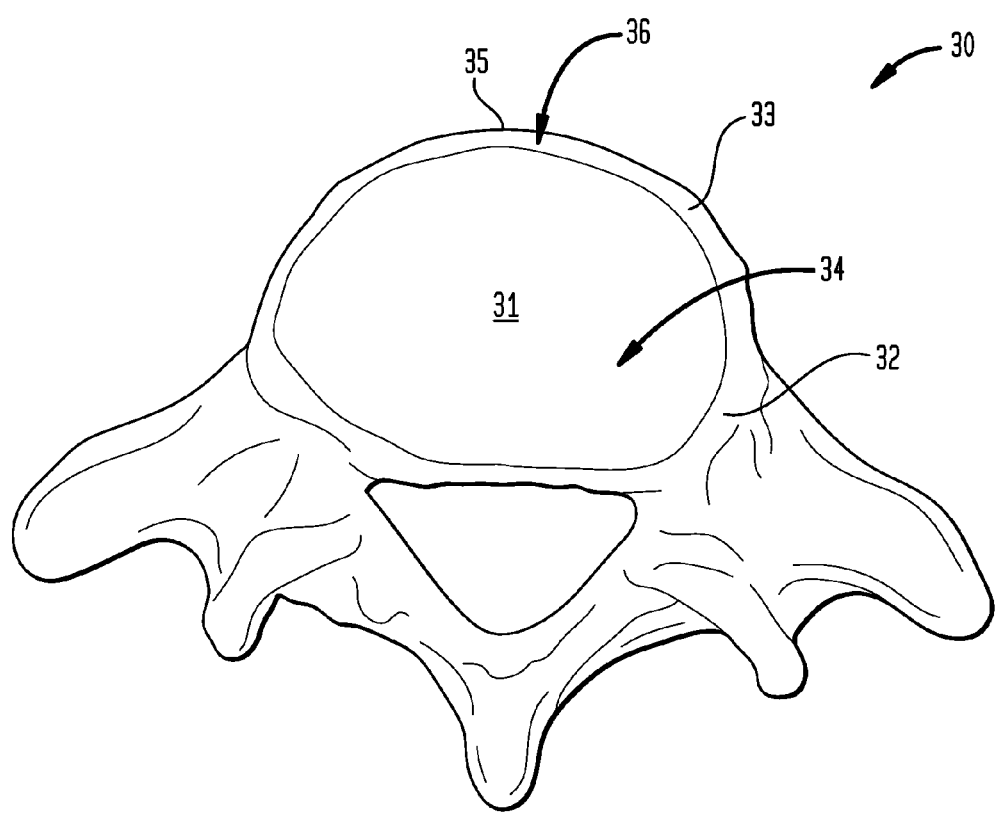
FIG. 2 is a top view of the inferior vertebra of FIG. 1.

One or more of chamfered sections 402, 404, 406, and 408 may include one or more chamfered interface ports 409 configured and arranged for releasably connecting to a positioning tool. Preferably, either or both of chamfered sections 402 and 404 associated with rear end 495 include a chamfered interface port 409, because spacer 400 is intended to be moved to the location of interest by directing the front of spacer 400 toward the end plate, such as end plate portion 34 shown in FIG. 2, by pushing on an area at or adjacent to rear end 495 of spacer 400, which may optionally include first side 415 and/or second side 425. The angles of each of chamfered sections 402, 404, 406, and 408 with respect to length axis L may all be the same. Alternatively, only certain of such angles may be the same, or they may each be different. Of course, any of chamfered sections 402, 404, 406, and 408 may also be angled with respect to width axis W and/or height axis H. Chamfered interface ports 409 establish non-axial, or off-axis, interfaces of spacer 400 in that they are not aligned or parallel with any major axis of the body of spacer 400. Chamfered interface ports 409 may be smooth bore holes, threaded holes, or slotted holes. Alternatively, spacer 400 may be constructed such that it includes one or more connecting elements in addition to or instead of chamfered interface ports 409 that may be a rod, a hook, or any other means rather than a port for releasably joining to a positioning tool.

Rear surface 490 preferably, but not necessarily, includes a rear interface port 491 configured and arranged for releasably connecting to a positioning tool. Rear interface port 491 may be a smooth bore hole, a threaded hole, or a slotted hole. Rear interface port 491 may or may not extend completely through spacer 400 from rear surface 490 to front surface 480. Alternatively, spacer 400 may be constructed such that it includes one or more connecting elements in addition to or instead of rear interface port 491 that may be a rod, a hook, or any other means rather than a port for releasably joining to a positioning tool. It is to be noted that front surface 480 may also optionally include such an interface (when rear interface port 491 does not extend all the way through), there may be fewer than or more than one interface at either or both of rear surface 490 and front surface 480, and there may be different numbers of connecting means at rear surface 490 and front surface 480.

It is to be noted that rear interface port 491 is an on-axis axial interface. That is, it is aligned or in parallel with primary longitudinal length axis L. In this instance, rear interface port 491 is an on-axis contact location. The distance from rear surface 490 to front surface 480 establishes the length of spacer 400. Placement of an interface on either rear surface 490 or front surface 480 is optional, but doing so provides the surgeon with flexibility in the course of spacer placement.

First side 415, and specifically first side surface 410, of spacer 400 optionally includes one or more first side interface ports 411 configured and arranged for releasably connecting to a positioning tool. Of course, the same could be true for second side 425 and second side surface 420. First side interface port 411 may be a smooth bore hole, a threaded hole, or a slotted hole. First side interface port 411 may or may not extend completely through from first side surface 410 to second side surface 420. Alternatively, spacer 400 may be constructed such that it includes one or more connecting elements in addition to or instead of first side interface port 411 that may be a rod, a hook, or any other means rather than a port for releasably joining to a positioning tool. It is to be noted that there may be fewer than or more than one interface at either or both of first side surface 410 and second side surface 420, and there may be different numbers of connecting means at first side surface 410 and second side surface 420.

First side interface port 411 is an off-axis axial interface. That is, it is not aligned or in parallel with length axis L. Rather, in this instance first side interface port 411 is parallel to non-primary width axis W. The distance from first side surface 410 to second side surface 420 establishes the width of spacer 400. Placement of an interface on either or both of first side surface 410 and second side surface 420 is optional, but doing so provides the surgeon with flexibility in the course of spacer placement.

An illustrative manner of using a spacer according to the present invention is now described, with particular reference to spacer 400. Initially, the surgeon preferably performs preliminary steps ordinarily carried out in the course of an IF procedure. When it is time to insert spacer 400 in the intervertebral disc space, a positioning tool, such as above-described positioning tool 200, is connected to spacer 400 at one of the interface ports described above. If the surgeon wishes to advance spacer 400 along its longitudinal axis, i.e., along an axis parallel to length L, the positioning tool is joined to spacer 400 at one of the on-axis positioning interfaces, such as rear interface port 491, for example. During insertion when the surgeon wishes to cause spacer 400 to turn at an angle or in a curving manner, the positioning tool may be released from its connection to the axial, or on-axis, port and re-connected to spacer 400 at an off-axis port. Of course, the positioning tool need not immediately be repositioned into a port; it may be used to manipulate spacer 400 from any of its exterior surfaces. Alternatively, the positioning tool may remain connected to spacer 400 and realigned in an off-axis manner at one of the off-axis positioning interfaces, such as chamfered interface port 409 of first chamfered section 402, for example. The surgeon may continue to advance spacer 400 by pushing on the positioning tool when it is connected to spacer 400 until it reaches a final selected location. Throughout such advancement, the orientation of the positioning tool may be changed with respect to spacer 400, wherein the surgeon disconnects the positioning tool from the off-axis interface and re-connects it to a different (preferably off-axis) interface, such as first side interface port 411 of first side surface 410, for example. The surgeon may use spacer 400 and the positioning tool to fine tune the placement of spacer 400 at a desired location through the use of one or more of the off-axis interfaces and, optionally, the on-axis interface. The surgeon may also wish to expand spacer 400 using any of the off-axis and on-axis interfaces.

The positioning tool 200 is preferably used to position the spacer substantially between the outer, dense portions of vertebrae, between which an intervertebral disc has been surgically removed, but is not limited thereto. Tip 232 is inserted into a selected interface port and releasably secured thereto. Retractable member 230 is then extended to force the spacer forward, either directly or at an angle or in a curved manner, dependent upon the interface port selected and the spacer design. Upon reaching a position of interest, tip 232 is released from its connection to the interface port, retractable member 230 is withdrawn, and tip 232 is moved to connect with another off-axis interface port. The process is repeated until the surgeon is satisfied that the spacer has been positioned substantially in the location of interest.

Therefore, spacer 400 may be positioned at desirable location 36 through the use of an axial or linear positioning tool, such as positioning tool 200. The positioning tool is preferably first aligned with an on-axis port of spacer 400 during initial insertion. After spacer 400 is maneuvered into the disc space, the positioning tool may be disconnected from the on-axis port and reconnected with one or more off-axis ports as necessary to further maneuver spacer 400 into desirable location 36. A spacer according to this embodiment of the present invention may also include a self-steering aspect which will allow spacer 400 to orient itself in the disc space while being aided in such orientation by the positioning tool. An advantageous aspect of this method is that the positioning tool may be utilized in a substantially posterior-anterior direction, which is due to its repeated disconnection and reconnection to the posterior-most facing port of spacer 400 as spacer 400 rotates into its final position. The results is a procedure that utilizes a standard or existing positioning tool in order to insert and rotate spacer 400.

FIGS. 19-22 illustrate another embodiment of an off-axis spacer 500 of the present invention. Spacer 500 is similar to spacer 400 of FIGS. 16-18, except that it is not symmetrical with respect to its forward design. That is, a top surface 530 of spacer 500 is not symmetrical with respect to any axis parallel to width axis W. Spacer 500 may be used in the same manner as that described with respect spacer 400. Spacer 500 includes top surface 530, a bottom surface 540 that is preferably a mirror image of top surface 530, first and second sides 515 and 525, respectively, which are mirror images of one another, a front end 585 and a rear end 595. First side 515 includes a first side surface 510, and second side 525 includes a second side surface 520. Similarly, front end 585 includes a front surface 580, and rear end 595 includes a rear surface 590. Top surface 530 includes an optional top interface port 531 configured and arranged for releasably connecting to a positioning tool, such as aforementioned positioning tool 200. Top interface port 531 may be a smooth bore hole, a threaded hole, or a slotted hole. Top interface port 531 may or may not extend completely through from top surface 530 to bottom surface 540. Alternatively, spacer 500 may be constructed such that it includes one or more connecting elements in addition to or instead of top interface port 531 that may be a rod, a hook, or any other means rather than a port for releasably joining to a positioning tool. It is to be noted that bottom surface 540 may also include such an interface, there may be fewer than or more than one interface at either or both of top surface 530 and bottom surface 540, and there may be different numbers of connecting means at top surface 530 and bottom surface 540. Spacer 500 may be fabricated as a unitary structure or it may be fabricated of a plurality of sections. It may be of fixed dimensions or expandable. It may be fabricated of one or more materials of interest, provided such material is selected to enable spacer 500 to perform for its intended purpose under the expected conditions.

It is to be noted that top interface port 531 is an off-axis axial interface aligned with non-primary height axis H of spacer 500. Top surface 530 and bottom surface 540 of spacer 500 are those surfaces that contact the adjacent vertebrae and establish the spacing surfaces of spacer 500 and their separation from one another establishes the height of spacer 500. Placement of an interface on either top surface 530 or bottom surface 540 is optional, but does provide the surgeon with flexibility in at least the initial stages of spacer placement. Of course, it is to be understood that there may be through holes (not shown) extending from top surface 530 to bottom surface 540 to allow for bone graft packing and growth therethrough to secure spacer 500 in position as part of the IF procedure.

Spacer 500 further includes a plurality of chamfered sections. First chamfered section 502 and second chamfered section 504 are located at rear end 595 of spacer 500. First chamfered section 502 is spaced from and connected to second chamfered section 504 by rear surface 590 of spacer 500. Front surface 580 is substantially parallel to rear surface 590, and front surface 580 is connected directly to first side surface 510 and second side surface 520, not by way of any chamfered sections.

One or both of first and second chamfered sections 502 and 504, respectively, may include one or more chamfered interface ports 509 configured and arranged for releasably connecting to a positioning tool. The angles of each of chamfered sections 502 and 504 with respect to length axis L may be the same or they may be different. Of course, any of chamfered sections 502 and 504 may also be angled with respect to width axis W and/or height axis H. Chamfered interface ports 509 establish non-axial interfaces of spacer 500 in that they are not aligned or parallel with any major axis of the body of spacer 500. Chamfered interface ports 509 may be smooth bore holes, threaded holes, or slotted holes. Alternatively, spacer 500 may be constructed such that it includes one or more connecting elements in addition to or instead of chamfered interface ports 509 that may be a rod, a hook, or any other means rather than a port for releasably joining to a positioning tool.

Rear surface 590 preferably, but not necessarily, includes a rear interface port 591 configured and arranged for releasably connecting to a positioning tool. Rear interface port 591 may be a smooth bore hole, a threaded hole, or a slotted hole. Rear interface port 591 may or may not extend completely through spacer 500 from rear surface 590 to front surface 580. Alternatively, spacer 500 may be constructed such that it includes one or more connecting elements in addition to or instead of rear interface port 591 that may be a rod, a hook, or any other means rather than a port for releasably joining to a positioning tool. It is to be noted that front surface 580 may also optionally include a front interface port 581 (when rear interface port 591 does not extend all the way through), there may be fewer than or more than one interface at either or both of rear surface 590 and front surface 580, and there may be different numbers of connecting means at rear surface 590 and front surface 580.

It is to be noted that rear interface port 591 and front interface port 581 are on-axis axial interfaces aligned or in parallel with primary longitudinal length axis L of spacer 500. The distance from rear surface 590 to front surface 580 establishes the length of spacer 500. Placement of an interface on either rear surface 590 or front surface 580 is optional, but doing so provides the surgeon with flexibility in the course of spacer placement.

First side 515, and specifically first side surface 510, of spacer 500 optionally includes one or more first side interface ports 511 configured and arranged for releasably connecting to a positioning tool. Of course, the same could be true for second side 525 and second side surface 520. First side interface port 511 may be a smooth bore hole, a threaded hole, or a slotted hole. First side interface port 511 may or may not extend completely through from first side surface 510 to second side surface 520. Alternatively, spacer 500 may be constructed such that it includes one or more connecting elements in addition to or instead of first side interface port 511 that may be a rod, a hook, or any other means rather than a port for releasably joining to a positioning tool. It is to be noted that there may be fewer than or more than one interface at either or both of first side surface 510 and second side surface 520, and there may be different numbers of connecting means at first side surface 510 and second side surface 520.

First side interface port 511 is an off-axis axial interface aligned or in parallel with non-primary width axis W of spacer 500. The distance from first side surface 510 to second side surface 520 establishes the width of spacer 500. Placement of one or more interfaces on either or both of first side surface 510 and second side surface 520 is optional, but doing so provides the surgeon with flexibility in the course of spacer placement.

FIGS. 23-26 illustrate another embodiment of an off-axis spacer 600 of the present invention. Spacer 600 is similar to spacer 500 of FIGS. 19-22, except that it is not symmetrical with respect to its rear design. That is, a top surface 630 of spacer 600 is not symmetrical with respect to any axis parallel to width axis W or length axis L. Spacer 600 may be used in the same manner as that described with respect to spacer 400. Spacer 600 includes a top surface 630, a bottom surface 640 that is preferably a mirror image of top surface 630, first and second sides 615 and 625, respectively, that are mirror images of one another, a front end 685 and a rear end 695. First side 615 includes a first side surface 610, and second side 625 includes a second side surface 620. Similarly, front end 685 includes a front surface 680, and rear end 695 includes a rear surface 690. Top surface 630 includes an optional top interface port 631 configured and arranged for releasably connecting to a positioning tool, such as aforementioned positioning tool 200. Top interface port 631 may be a smooth bore hole, a threaded hole, or a slotted hole. Top interface port 631 may or may not extend completely through from top surface 630 to bottom surface 640. Alternatively, spacer 600 may be constructed such that it includes one or more connecting elements in addition to or instead of top interface port 631 that may be a rod, a hook, or any other means rather than a port for releasably joining to a positioning tool. It is to be noted that bottom surface 640 may also include such an interface, there may be fewer than or more than one interface at either or both of top surface 630 and bottom surface 640, and there may be different numbers of connecting means at top surface 630 and bottom surface 640. Spacer 600 may be fabricated as a unitary structure or it may be fabricated of a plurality of sections. It may be of fixed dimensions or expandable. It may be fabricated of one or more materials of interest, provided such material is selected to enable spacer 600 to perform for its intended purpose under the expected conditions.

It is to be noted that top interface port 631 is an off-axis axial interface aligned with non-primary height axis H of spacer 600. Top surface 630 and bottom surface 640 of spacer 600 are those surfaces that contact the adjacent vertebrae and establish the spacing surfaces of spacer 600 and their separation from one another establishes the height of spacer 600. Placement of an interface on either top surface 630 or bottom surface 640 is optional, but does provide the surgeon with flexibility in at least the initial stages of spacer placement. Of course, it is to be understood that there may be through holes (not shown) extending from top surface 630 to bottom surface 640 to allow for bone graft packing and growth therethrough to secure spacer 600 in position as part of the IF procedure.

Spacer 600 further includes chamfered section 602 located at rear end 695 of spacer 600. Chamfered section 602 extends from rear surface 690 to first side surface 610. Front surface 680 is substantially parallel to rear surface 690, and front surface 680 is connected directly to first side surface 610 and second side surface 620, not by way of any chamfered sections.

Chamfered section 602 includes a chamfered interface port 609 configured and arranged for releasably connecting to a positioning tool. The angle of the chamfered section 602 with respect to length axis L is selectable. Of course, chamfered sections 602 may also be angled with respect to width axis W and/or height axis H. Chamfered interface port 609 establishes a non-axial interface of spacer 600 in that it is not aligned or parallel with any major axis of the body of spacer 600. Chamfered interface port 609 may be a smooth bore hole, a threaded hole, or a slotted hole. Alternatively, spacer 600 may be constructed such that it includes one or more connecting elements in addition to or instead of chamfered interface port 609 that may be a rod, a hook, or any other means rather than a port for releasably joining to a positioning tool.

Rear surface 690 preferably, but not necessarily, includes a rear interface port 691 configured and arranged for releasably connecting to a positioning tool. Rear interface port 691 may be a smooth bore hole, a threaded hole, or a slotted hole. Rear interface port 691 may or may not extend completely through spacer 600 from rear surface 690 to front surface 680. Alternatively, spacer 600 may be constructed such that it includes one or more connecting elements in addition to or instead of rear interface port 691 that may be a rod, a hook, or any other means rather than a port for releasably joining to a positioning tool. It is to be noted that front surface 680 may also optionally include a front interface port 681 (when rear interface port 691 does not extend all the way through), there may be fewer than or more than one interface port at either or both of rear surface 690 and front surface 680, and there may be different numbers of connecting means at rear surface 690 and front surface 680.

It is to be noted that rear interface port 691 and front interface port 681 are on-axis axial interfaces aligned or in parallel with primary longitudinal length axis L of spacer 600. The distance from rear surface 690 to front surface 680 establishes the length of spacer 600. Placement of an interface on either rear surface 690 or front surface 680 is optional, but doing so provides the surgeon with flexibility in the course of spacer placement.

First side 615, and specifically first side surface 610, of spacer 600 optionally includes one or more first side interface ports 611 configured and arranged for releasably connecting to a positioning tool. Of course, the same could be true for second side 625 and second side surface 620. First side interface port 611 may be a smooth bore hole, a threaded hole, or a slotted hole. First side interface port 611 may or may not extend completely through from first side surface 610 to second side surface 620. Alternatively, spacer 600 may be constructed such that it includes one or more connecting elements in addition to or instead of first side interface port 611 that may be a rod, a hook, or any other means rather than a port for releasably joining to a positioning tool. It is to be noted that there may be fewer than or more than one interface at either or both of first side surface 610 and second side surface 620, and there may be different numbers of connecting means at first side surface 610 and second side surface 620.

First side interface port 611 is an off-axis axial interface aligned or in parallel with the non-primary width axis W of spacer 600. The distance from first side surface 610 to second side surface 620 establishes the width of spacer 600. Placement of one or more interface ports on either or both of the first side surface 610 and second side surface 620 is optional, but doing so provides the surgeon with flexibility in the course of spacer placement.

Figure 28:
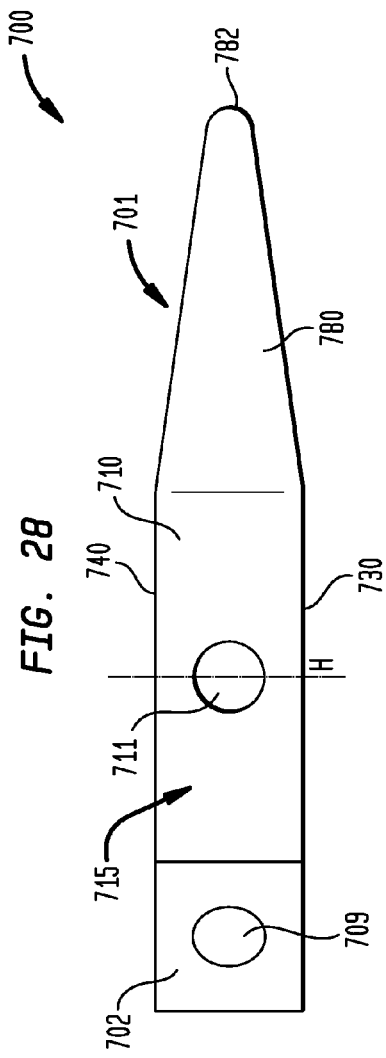
FIG. 28 is a first side view of the spacer of FIG. 27, the second side being a mirror image thereof.
Figure 27:
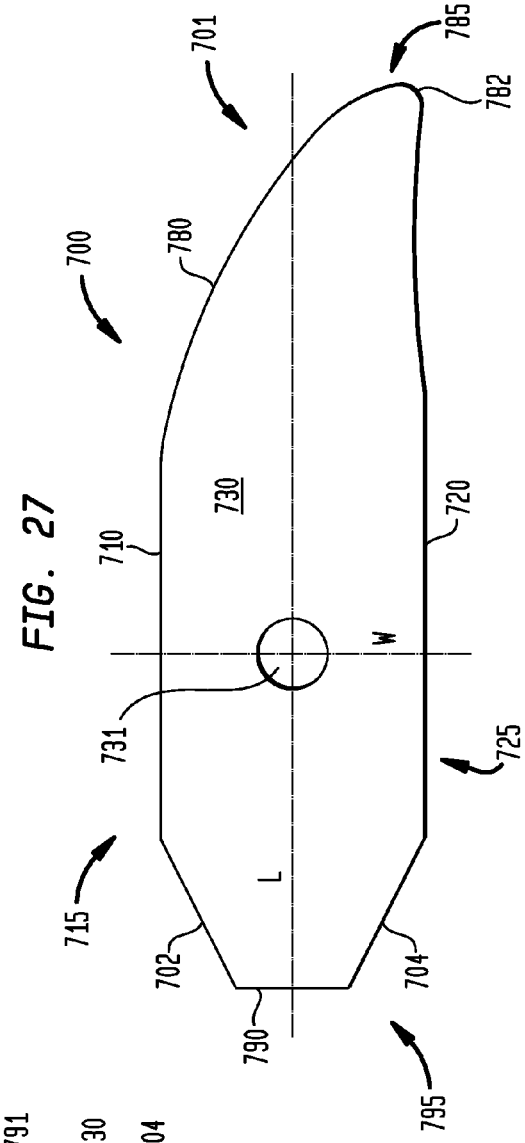
FIG. 27 is a top view of another embodiment of a spacer of the present invention, the bottom being a mirror image thereof.
Figure 29:
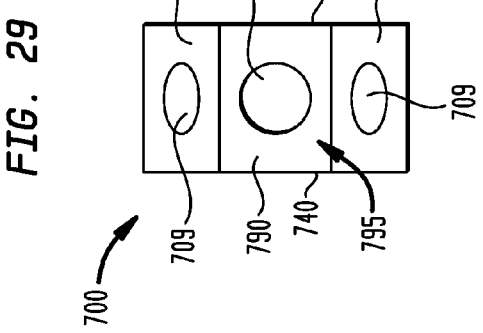
FIG. 29 is a rear view of the spacer of FIG. 27.

FIGS. 27-29 illustrate another embodiment of an off-axis spacer 700 of the present invention. Spacer 700 is similar to spacer 500 of FIGS. 19-22, except that it has a curved forward design 701. Spacer 700 may be used in the same manner as that described with respect to spacer 400, although curved forward design 701 enables curving movement of spacer 700 more readily than may be achieved with any other spacer embodiments herein described. Spacer 700 includes a top surface 730, a bottom surface 740 that is preferably a mirror image of top surface 730, first and second sides 715 and 725, respectively, a front end 785 and a rear end 795. First side 715 includes a first side surface 710, and second side 725 includes a second side surface 720. Similarly, front end 785 includes a front surface 780, and rear end 795 includes a rear surface 790. Top surface 730 includes an optional top interface port 731 configured and arranged for releasably connecting to a positioning tool, such as aforementioned positioning tool 200. Top interface port 731 may be a smooth bore hole, a threaded hole, or a slotted hole. Top interface port 731 may or may not extend completely through from top surface 730 to bottom surface 740. Alternatively, spacer 700 may be constructed such that it includes one or more connecting elements in addition to or instead of top interface port 731 that may be a rod, a hook, or any other means rather than a port for releasably joining to a positioning tool. It is to be noted that bottom surface 740 may also include such an interface, there may be fewer than or more than one interface at either or both of top surface 730 and bottom surface 740, and there may be different numbers of connecting means at top surface 730 and bottom surface 740. Spacer 700 may be fabricated as a unitary structure or it may be fabricated of a plurality of sections. It may be of fixed dimensions or expandable. It may be fabricated of one or more materials of interest, provided such material is selected to enable spacer 700 to perform for its intended purpose under the expected conditions.

It is to be noted that top interface port 731 is an off-axis axial interface aligned with non-primary height axis H of spacer 700. Top surface 730 and bottom surface 740 of spacer 700 are those surfaces that contact the adjacent vertebrae and establish the spacing surfaces of spacer 700 and their separation from one another establishes the height of spacer 700. Placement of an interface on either top surface 730 or bottom surface 740 is optional, but does provide the surgeon with flexibility in at least the initial stages of spacer placement. Of course, it is to be understood that there may be through holes (not shown) extending from top surface 730 to bottom surface 740 to allow for bone graft packing and growth therethrough to secure spacer 700 in position as part of the IF procedure.

Spacer 700 further includes a plurality of chamfered sections. First chamfered section 702 and second chamfered section 704 are located at rear end 795 of spacer 700. First chamfered section 702 is spaced from and connected to second chamfered section 704 by rear surface 790 of spacer 700. Front end 780 is arranged to enable steerable movement of spacer 700 to a location of interest, such as desirable location 36. In the embodiment shown in FIGS. 27-29, front end 780 includes curved forward design 701, which may be of different configuration provided it undertakes curving movement when spacer 700 is pushed with a positioning tool. Curved forward design 701 may also be beveled or otherwise shaped to increase its friction with respect to the surface of end plate on which it rides so that it is inclined to dig into the end plate and be forced to turn in a direction associated with the direction of its curved form. That is, the curved form of front end 780 is preferably configured to produce greater friction between the end plate and the remaining portions of the body of spacer 700, including rear end 795.

One or both of first and second chamfered sections 702 and 704, respectively, may include one or more chamfered interface ports 709 configured and arranged for releasably connecting to a positioning tool. The angles of each of chamfered sections 702 and 704 with respect to length axis L may be the same or they may be different. Of course, any of chamfered sections 702 and 704 may also be angled with respect to width axis W and/or height axis H. Chamfered interface ports 709 establish non-axial, or off-axis, interfaces of spacer 700 in that they are not aligned or parallel with any major axis of the body of spacer 700. Chamfered interface ports 709 may be smooth bore holes, threaded holes, or slotted holes. Alternatively, spacer 700 may be constructed such that it includes one or more connecting elements in addition to or instead of chamfered interface ports 709 that may be a rod, a hook, or any other means rather than a port for releasably joining to a positioning tool.

Rear surface 790 preferably, but not necessarily, includes a rear interface port 791 configured and arranged for releasably connecting to a positioning tool. Rear interface port 791 may be a smooth bore hole, a threaded hole, or a slotted hole. Rear interface port 791 may or may not extend completely through spacer 700 from rear surface 790 to front surface 780 of spacer 700. Alternatively, spacer 700 may be constructed such that it includes one or more connecting elements in addition to or instead of rear interface port 791 that may be a rod, a hook, or any other means rather than a port for releasably joining to a positioning tool. There may be fewer than or more than one interface at rear surface 790.

It is to be noted that rear interface port 791 is an on-axis interface and is aligned or in parallel with primary longitudinal length axis L of spacer 700. The distance from rear surface 790 to an end 782 of front end 780 establishes the length of spacer 700. Placement of an interface on rear surface 790 is optional, but doing so provides the surgeon with flexibility in the course of spacer placement.

First side 715 and specifically first side surface 710, of spacer 700 optionally includes one or more first side interface ports 711 configured and arranged for releasably connecting to a positioning tool. Of course, the same could be true for second side 725 and second side surface 720. First side interface port 711 may be a smooth bore hole, a threaded hole, or a slotted hole. First side interface port 711 may or may not extend completely through from first side surface 710 to second side surface 720. Alternatively, spacer 700 may be constructed such that it includes one or more connecting elements in addition to or instead of first side interface port 711 that may be a rod, a hook, or any other means rather than a port for releasably joining to a positioning tool. It is to be noted that there may be fewer than or more than one interface at either or both of first side surface 710 and second side surface 720, and there may be different numbers of connecting means at first side surface 710 and second side surface 720.

First side interface port 711 is an off-axis axial interface aligned or in parallel with non-primary width axis W of spacer 700. The distance from first side surface 710 to second side surface 720 establishes the width of spacer 700. Placement of one or more interfaces on either or both of first side surface 710 and second side surface 720 is optional, but doing so provides the surgeon with flexibility in the course of spacer placement.

An embodiment of an off-axis expandable spacer 800 of the present invention is shown in FIGS. 30-33. Spacer 800 is similar to spacer 500 of FIGS. 19-22, except that it is expandable rather than of static dimensions. That is, the size and shape of spacer 800 may be modified by the surgeon, preferably during a surgical procedure. Spacer 800 may be used in the same manner as that described with respect to any of the above-described spacers. In addition to the ability to adjust the positioning of spacer 800 in an on-axis manner, the size and shape of spacer 800 may also be modified through off-axis manipulation. Spacer 800 includes a top surface 830, a bottom surface 840 that is preferably a mirror image of top surface 830, first and second sides 815 and 825, respectively, that are mirror images of one another, a front end 885 and a rear end 895. First side 815 includes a first side surface 810, and second side 825 includes a second side surface 820. Similarly, front end 885 includes a front surface 880, and rear end 895 includes a rear surface 890. Top surface 830 includes an optional top interface port 831 configured and arranged for releasably connecting to a positioning tool, such as aforementioned positioning tool 200. Top interface port 831 may be a smooth bore hole, a threaded hole, or a slotted hole. Top interface port 831 may or may not extend completely through from top surface 830 to bottom surface 840. Alternatively, spacer 800 may be constructed such that it includes one or more connecting elements in addition to or instead of top interface port 831 that may be a rod, a hook, or any other means rather than a port for releasably joining to the positioning tool. It is to be noted that bottom surface 840 may also include such an interface, there may be fewer than or more than one interface at either or both of top surface 830 and bottom surface 840, and there may be different numbers of connecting means at top surface 830 and bottom surface 840. Spacer 800 may be fabricated as a unitary structure or it may be fabricated of a plurality of sections. It may be fabricated of one or more materials of interest, provided such material is selected to enable spacer 800 to perform for its intended purpose under the expected conditions.

It is to be noted that top interface port 831 is an off-axis axial interface aligned with non-primary height axis H of spacer 800. Top surface 830 and bottom surface 840 of spacer 800 are those faces that contact the adjacent vertebrae and establish the spacing surfaces of spacer 800 and their separation from one another establishes the height of spacer 800. Placement of an interface on either top surface 830 or bottom surface 840 is optional, but does provide the surgeon with flexibility in at least the initial stages of spacer placement. Of course, it is to be understood that there may be through holes (not shown) extending from top surface 830 to bottom surface 840 to allow for bone graft packing and growth therethrough to secure spacer 800 in position as part of the IF procedure.

Spacer 800 further includes a plurality of chamfered sections. First chamfered section 802 and second chamfered section 804 are located at rear end 895 of spacer 800. First chamfered section 802 is spaced from and connected to second chamfered section 804 by rear surface 890 of spacer 800. Front surface 880 is substantially parallel to rear surface 890, and front surface 880 is connected directly to first side surface 810 and second side surface 820, not by way of any chamfered sections.

One or both of first and second chamfered sections 802 and 804, respectively, may include one or more chamfered interface ports 809 configured and arranged for releasably connecting to a positioning tool. The angles of each of chamfered sections 802 and 804 with respect to length axis L may be the same or they may be different. Of course, any of chamfered sections 802 and 804 may also be angled with respect to width axis W and/or height axis H. Chamfered interface ports 809 establish non-axial or off-axis interfaces of spacer 800 in that they are not aligned or parallel with any major axis of the body of spacer 800. Chamfered interface ports 809 may be smooth bore holes, threaded holes, or slotted holes. Alternatively, spacer 800 may be constructed such that it includes one or more connecting elements in addition to or instead of chamfered interface ports 809 that may be a rod, a hook, or any other means rather than a port for releasably joining to a positioning tool.

Figure 31:
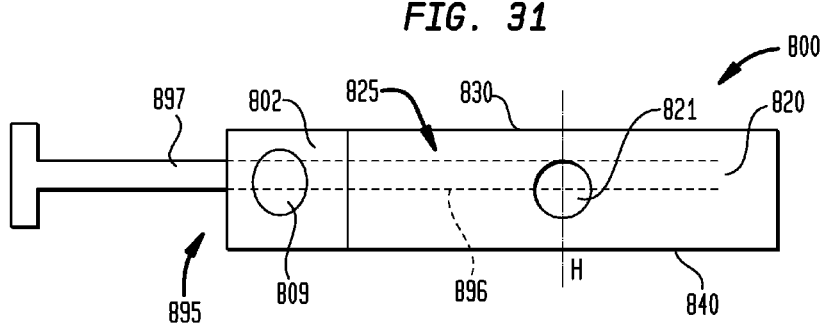
FIG. 31 is a second side view of the expandable spacer of FIG. 30 in an unexpanded configuration, the first side being a mirror image thereof.
Figure 30:
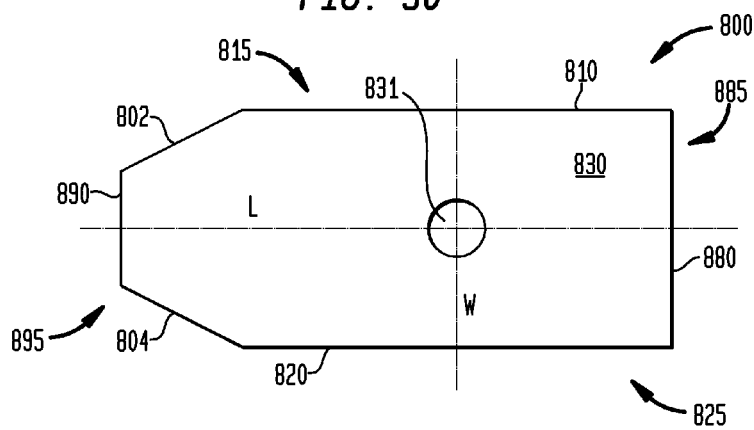
FIG. 30 is a top view of an expandable embodiment of a spacer of the present invention in an unexpanded configuration, the bottom being a mirror image thereof.
Figure 33:
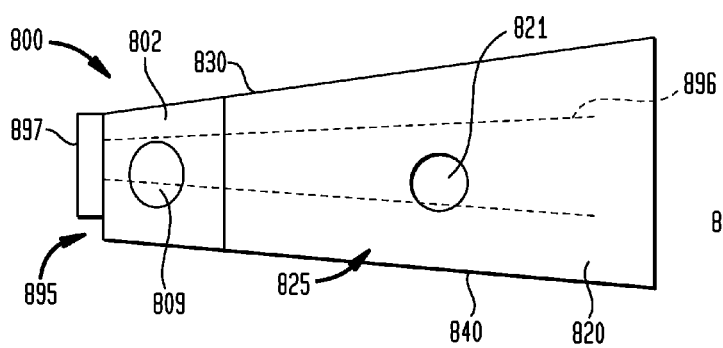
FIG. 33 is second side view of the expandable spacer of FIG. 30 in an expanded configuration, the first side being a mirror image thereof.
Figure 32:
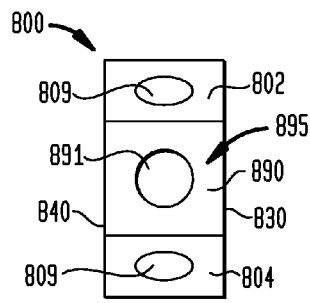
FIG. 32 is a rear view of the expandable spacer of FIG. 30.

Rear surface 890 preferably, but not necessarily, includes a rear interface port 891 configured and arranged for releasably connecting to a positioning tool, or as shown in FIGS. 31 and 33, an expander 897. Rear interface port 891 may be a smooth bore hole, a threaded hole, or a slotted hole. Rear interface port 891 may or may not extend completely through spacer 800 from rear surface 890 to front surface 880 of spacer 800. There may be fewer than or more than one interface at rear surface 890.

It is to be noted that rear interface port 891 is an on-axis interface and is aligned or in parallel with primary longitudinal length axis L of spacer 800. The distance from rear surface 890 to an end 882 of front end 880 establishes the length of spacer 800. Placement of an interface on rear surface 890 is optional, but doing so provides the surgeon with flexibility in the course of spacer placement and/or expansion.

First side 815 and specifically first side surface 810, of spacer 800 optionally includes one or more first side interface ports 811 configured and arranged for releasably connecting to a positioning tool. Of course, the same could be true for second side 825 and second side surface 820. First side interface port 811 may be a smooth bore hole, a threaded hole, or a slotted hole. First side interface port 811 may or may not extend completely through from first side surface 810 to second side surface 820. Alternatively, spacer 800 may be constructed such that it includes one or more connecting elements in addition to or instead of first side interface port 811 that may be a rod, a hook, or any other means rather than a port for releasably joining to the positioning tool. It is to be noted that there may be fewer than or more than one interface at either or both of first side surface 810 and second side surface 820, and there may be different numbers of connecting means at first side surface 810 and second side surface 820.

First side interface port 811 is an off-axis axial interface aligned or in parallel with non-primary width axis W of spacer 800. The distance from first side surface 810 to second side surface 820 establishes the width of spacer 800. Placement of one or more interfaces on either or both of first side surface 810 and second side surface 820 is optional, but doing so provides the surgeon with flexibility in the course of spacer placement.

As spacer 800 is expandable, it includes means for its expansion. Further shown in FIGS. 30-33, the spacer 800 includes an expansion channel 896 extending partially through from rear end 895. Expansion channel 896 may coincide with rear interface port 891 or may be separate therefrom. It may optionally extend all the way through to front end 885 of spacer 800. Although shown as an on-axis expansion channel, it is to be understood that expansion channel

896 may be of an off-axis arrangement. That is, expansion channel 896 may be located at an off-axis position. Moreover, it is contemplated that any of the interfaces herein, both on-axis and off-axis, may be coincident with an expansion channel similar to expansion channel 896. An expansion channel according to the present invention may thusly be of an on-axis or an off-axis arrangement, and more than one expansion channel may be provided in a spacer. Spacer 800 further includes expander 897 arranged for removable or permanent insertion into expansion channel 896. Expansion channel 896 and expander 897 are arranged such that when expander 897 is directed into expansion channel 896, the shape and size of spacer 800 may be changed. For example, as shown in FIG. 33, substantially complete insertion of expander 897 into expansion channel 896 causes top surface 830 and bottom surface 840 of spacer 800 to move apart to produce a wedge shape of spacer 800. In this example, expansion channel 896 is threaded and expander 897 is a screw that may be threaded into threaded expansion channel 896. However, expansion channel 896 may be smooth and expander 897 may similarly have a smooth exterior. In particular, with expansion channel 896 in a wedged shape, spacer 800 will become wedge-shaped. Alternatively, expansion channel 896 may be of uniform dimensions, resulting in uniform and parallel increased separation of top surface 830 and bottom surface 840. Those of ordinary skill in the art will recognize that other means of expansion may be achieved including, but not limited to, the use of wedges, cams, or the like. It is also contemplated that a removable tool be used for expansion in lieu of the permanently-implanted expander 897.

In use, expandable spacer 800 may be positioned at a selectable angle with respect to the posterior-anterior axis of the disc space as desired, based on the selection and utilization of one or more of the on-axis and/or off-axis ports described above for interfacing with the positioning tool. The positioning tool or another tool configured with an interface releasably connectable to expander 897 may be used for any of the above-described modification. The expansion of spacer 800 may occur before, during or after its positioning. The expansion may occur partially or completely at any of those instances. As noted, expansion channel 896 may be configured in an on-axis or an off-axis design and the expansion tool may be adaptable for interfacing in either configuration.

Positioning spacer 800 according to the above-described method of insertion preferably exposes at least one off-axis interface of spacer 800 generally to the posterior incision site for manipulation either during implantation or after spacer 800 is finally positioned. Thus, in addition to utilizing the at least one off-axis interface for positioning spacer 800, the at least one off-axis interface may also be utilized for purposes of expansion, manipulation, or other types of modification pertaining to the size, dimension and/or shape of spacer 800. This modification may occur after spacer 800 has been finally positioned in an anterior aspect of the disc space. Such modification may also or alternatively occur at any point during the insertion process. For instance, spacer 800 may be inserted to a certain position, expanded to a determined height, and further inserted and expanded as necessary. The ability to modify spacer 800 at an off-axis interface gives the surgeon greater control of the surgical procedure, and allows the surgeon to more finely position and modify spacer 800 according to the particular parameters of the patient and the surgical procedure.

Although it is preferable that a port coinciding with a surface of the spacer be of a cylindrical nature having an axis normal to such surface, it is contemplated that any interface herein described can be offset from an axis normal to such surface. For example, a port located on a chamfered surface may be normal to any of the front, rear, or side surfaces. This would allow for a configuration of spacer 400, for example, where two or three of the ports accessible from rear end 495 are oriented in an on-axis manner.

The present invention has been described with respect to various embodiments. Nevertheless, it is to be understood that various modifications may be made without departing from the spirit and scope of the invention. All equivalents are deemed to fall within the scope of this description of the invention.

The invention claimed is:

1. A method of inserting and positioning a prosthetic intervertebral spacer in the intervertebral disc space between two adjacent vertebrae, the method comprising the steps of:
   providing a spacer including a longitudinal axis, a first interface, and a second interface;
   engaging a tool to the first interface;
   inserting the spacer at least partially into the intervertebral disc space by moving the tool substantially along an insertion direction;
   disengaging the tool from the spacer;
   engaging the tool to the second interface;
   inserting the spacer further into the intervertebral disc space by moving the tool substantially along the insertion direction, such that the longitudinal axis of the spacer is angled with respect to the insertion direction; and
   modifying the shape of the spacer by expanding the spacer.

2. The method of claim 1, wherein the insertion direction is substantially parallel to a posterior-anterior axis of the intervertebral disc space.

3. The method of claim 1, wherein the combination of the inserting steps results in the longitudinal axis of the spacer being perpendicular to the insertion direction.

4. The method of claim 3, wherein the longitudinal axis of the spacer is substantially parallel to a medial-lateral axis of the intervertebral disc space.

5. The method of claim 1, wherein the inserting steps result in the spacer being positioned in an anterior aspect of the intervertebral disc space.

6. The method of claim 1, wherein the inserting steps include allowing the spacer to rotate with respect to the insertion direction.

7. The method of claim 6, wherein the spacer further includes a front end having frictional properties that are greater than frictional properties of a rear end of the spacer, and wherein the inserting steps include allowing the front end to turn within the intervertebral disc space as it frictionally engages one or both of the adjacent vertebrae.

8. The method of claim 1, wherein the first interface and the second interface are ports, the tool includes a retractable member, and the engaging steps include placing the retractable member in the respective ports.

9. The method of claim 1, wherein the combination of the inserting steps results in the longitudinal axis of the spacer being rotated approximately 90 degrees with respect to the insertion direction.

10. The method of claim 1, further comprising the step of packing bone grafting material into at least one of the first interface, the second interface, and an opening in the spacer.

11. A method of inserting and positioning a prosthetic intervertebral spacer in the intervertebral disc space between two adjacent vertebrae, the method comprising the steps of:
    providing a spacer including a curved front end, a longitudinal axis, a first interface, and a second interface;

establishing a connection between a tool and the first interface of the spacer such that the tool and the spacer cannot substantially pivot with respect to one another;

inserting the spacer at least partially into the intervertebral disc space by moving the tool substantially along an insertion direction;

relocating the connection to the second interface such that the tool and the spacer cannot substantially pivot with respect to one another; and inserting the spacer further into the intervertebral disc space by moving the tool substantially along the insertion direction, such that the spacer rotates with respect to the insertion direction.

12. The method of claim 11, wherein the combination of the inserting steps results in the longitudinal axis of the spacer being perpendicular to the insertion direction.

13. The method of claim 11, wherein the inserting steps result in the spacer being positioned in an anterior aspect of the intervertebral disc space.

14. The method of claim 11, wherein the spacer further includes a front end having frictional properties that are greater than frictional properties of a rear end of the spacer, and wherein the inserting steps include allowing the front end to turn within the intervertebral disc space as it frictionally engages one or both of the adjacent vertebrae.

15. The method of claim 11, wherein the first interface and the second interface are ports, the tool includes a retractable member, and the establishing step includes placing the retractable member in the respective ports.

16. The method of claim 11, further comprising the step of modifying the shape of the spacer by expanding the spacer.

17. A method of inserting and positioning a prosthetic intervertebral spacer in the intervertebral disc space between two adjacent vertebrae, the method comprising the steps of:

providing a spacer including a longitudinal axis, a first interface, and a second interface;

applying a first force to the first interface to move the spacer in the intervertebral disc space;

applying a second force to the second interface to further move the spacer in the intervertebral disc space; and modifying the shape of the spacer by expanding the spacer, wherein the first and second forces are provided by a tool moving substantially along a single direction and cause the spacer to rotate, and wherein the tool is disengaged from the spacer between the step of applying the first force and the step of applying the second force.

18. The method of claim 17, wherein the spacer further includes a front end having frictional properties that are greater than frictional properties of a rear end of the spacer, and wherein the applying steps include allowing the front end to turn within the intervertebral disc space as it frictionally engages one or both of the adjacent vertebrae.

* * * * *